(12) United States Patent
Trumpp et al.

(10) Patent No.: US 11,591,658 B2
(45) Date of Patent: Feb. 28, 2023

(54) METHODS FOR SUB-TYPING AND TREATING CANCER

(71) Applicant: HI-STEM gGmbH, Heidelberg (DE)

(72) Inventors: Andreas Trumpp, Heidelberg (DE); Simon Raffel, Heidelberg (DE); Mattia Falcone, Heidelberg (DE)

(73) Assignee: HI-STEM gGmbH, Heidelberg (DE)

( * ) Notice: Subject to any disclaimer, the term of this patent is extended or adjusted under 35 U.S.C. 154(b) by 285 days.

(21) Appl. No.: 16/482,649

(22) PCT Filed: Jan. 31, 2018

(86) PCT No.: PCT/EP2018/052410
§ 371 (c)(1),
(2) Date: Jul. 31, 2019

(87) PCT Pub. No.: WO2018/141796
PCT Pub. Date: Aug. 9, 2018

(65) Prior Publication Data
US 2019/0382851 A1 Dec. 19, 2019

(30) Foreign Application Priority Data
Feb. 1, 2017 (EP) .................................. 17154260

(51) Int. Cl.
  C07H 21/02 (2006.01)
  C07H 21/04 (2006.01)
  *C12Q 1/6886* (2018.01)
  *A61P 35/02* (2006.01)
  *A61K 31/194* (2006.01)
  *C12N 15/113* (2010.01)

(52) U.S. Cl.
  CPC .......... *C12Q 1/6886* (2013.01); *A61K 31/194* (2013.01); *A61P 35/02* (2018.01); *C12N 15/1137* (2013.01); *C12N 2310/11* (2013.01); *C12N 2310/122* (2013.01); *C12N 2310/14* (2013.01); *C12N 2310/531* (2013.01); *C12Q 2600/106* (2013.01); *C12Q 2600/112* (2013.01); *C12Q 2600/156* (2013.01); *C12Q 2600/158* (2013.01)

(58) Field of Classification Search
  CPC .................................................. C12N 15/113
  See application file for complete search history.

(56) References Cited

U.S. PATENT DOCUMENTS

2005/0202451 A1* 9/2005 Burczynski .......... C12Q 1/6809
                                                       435/6.12
2016/0368862 A1 12/2016 Papathanassiu

FOREIGN PATENT DOCUMENTS

WO    2011141153 A1   11/2011
WO    2012100957 A1   8/2012

OTHER PUBLICATIONS

Elbashir et al. (The EMBO Journal, vol. 20, No. 23, pp. 6877-6888, 2001).*
MacKenzie, et al., "Cell-Permeating alpha-Ketoglutarate Derivatives Alleviate Pseudohypoxia in Succinate Dehydrogenase-Deficient Cells", Molecular and Cellular Biology, May 2007, p. 3282-3289.
Zdzisinska Barbara et al, "Alpha-Ketoglutarate as a Molecule with Pleiotropic Activity: Well-Known and Novel Possibilities of Therapeutic Use", Jun. 20, 2016 (Jun. 20, 2016), vol. 65, No. 1, p. 21-36, XP036139563.
J. Kim et al., "Silencing a Metabolic Oncogene", SCIENCE,vol. 340, No. 6132, May 3, 2013 (May 3, 2013), p. 558-559, XP055082474.
Patrick S. Ward et al., "The Common Feature of Leukemia-Associated IDH1 and IDH2 Mutations Is a Neomorphic Enzyme Activity Converting [alpha]-Ketoglutarate to 2-Hydroxyglutarate", Cancer Cell,vol. 17, No. 3, Mar. 1, 2010 (Mar. 1, 2010), p. 225-234, XP055007472.
M. M. Chaumeil et al., "Hyperpolarized [1-13C] Glutamate: A Metabolic Imaging Biomarker of IDH1 Mutational Status in Glioma", Cancer Research—Proceedings of the 106th Annual Meeting of the American Association for Cancer Research, Apr. 18-22, 2015; Philadelphia, PA,vol. 74, No. 16, May 29, 2014 (May 29, 2014), p. 4247-4257, XP055371964.
Martje Tönjes et al., "BCAT1 promotes cell proliferation through amino acid catabolism in gliomas carrying wild-type IDH1", Nature Medicine,vol. 19, No. 7, Jun. 23, 2013 (Jun. 23, 2013), p. 901-908, XP055252145.
Xie Fanfan et al., "Bipartite network analysis reveals metabolic gene expression profiles that are highly associated with the clinical outcomes of acute myeloid leukemia", Computational Biology and Chemistry, Elsevier, Amsterdam, NL,vol. 67, Jan. 6, 2017 (Jan. 6, 2017), p. 150-157, XP029926268.
Lorsbach Robert B et al, "TET1, a Member of a Novel Protein Family, Is Fused to MLL in Acute Myeloid Leukemia Containing the t(10;11)(q22;q23)", Blood, the American Society of Hematology, US,vol. 100, Nov. 16, 2002 (Nov. 16, 2002), p. 637-642, XP002502621.
Belicchi Ferrari Marisa et al., "Synthesis, characterization and biological activity of two new polymeric copper (II) complexes with alpha-ketoglutaric acid thiosemicarbazone.", Journal of Inorganic Biochemistry Apr. 10, 2002,vol. 89, No. 1-2,Apr. 10, 2002 (Apr. 10, 2002), p. 36-44, XP002770108.
Written Opinion of the International Searching Authority (ISA/237) issued in PCT/EP2018/052410 dated Jan. 31, 2018.
Nowicki et al., FEBS J 282 (2015) 2796-2805.
Chou et al., Blood 118 (2011) 3803-3810.

* cited by examiner

*Primary Examiner* — Amy H Bowman
(74) *Attorney, Agent, or Firm* — Prismatic Law Group, PLLC; Ronald J. Kamis

(57) ABSTRACT

This invention relates to a novel approach for the identification and stratification of subtypes of cancer, particularly subtypes of cancer characterized by an increased expression of BCAT1, particularly Acute Myeloid Leukemia (AML). The invention furthermore relates to a novel approach with respect to the treatment of cancer, particularly subtypes of cancer characterized by an increased expression of BCAT1, particularly Acute Myeloid Leukemia (AML).

7 Claims, 22 Drawing Sheets

Specification includes a Sequence Listing.

Figure 2 (contd.):
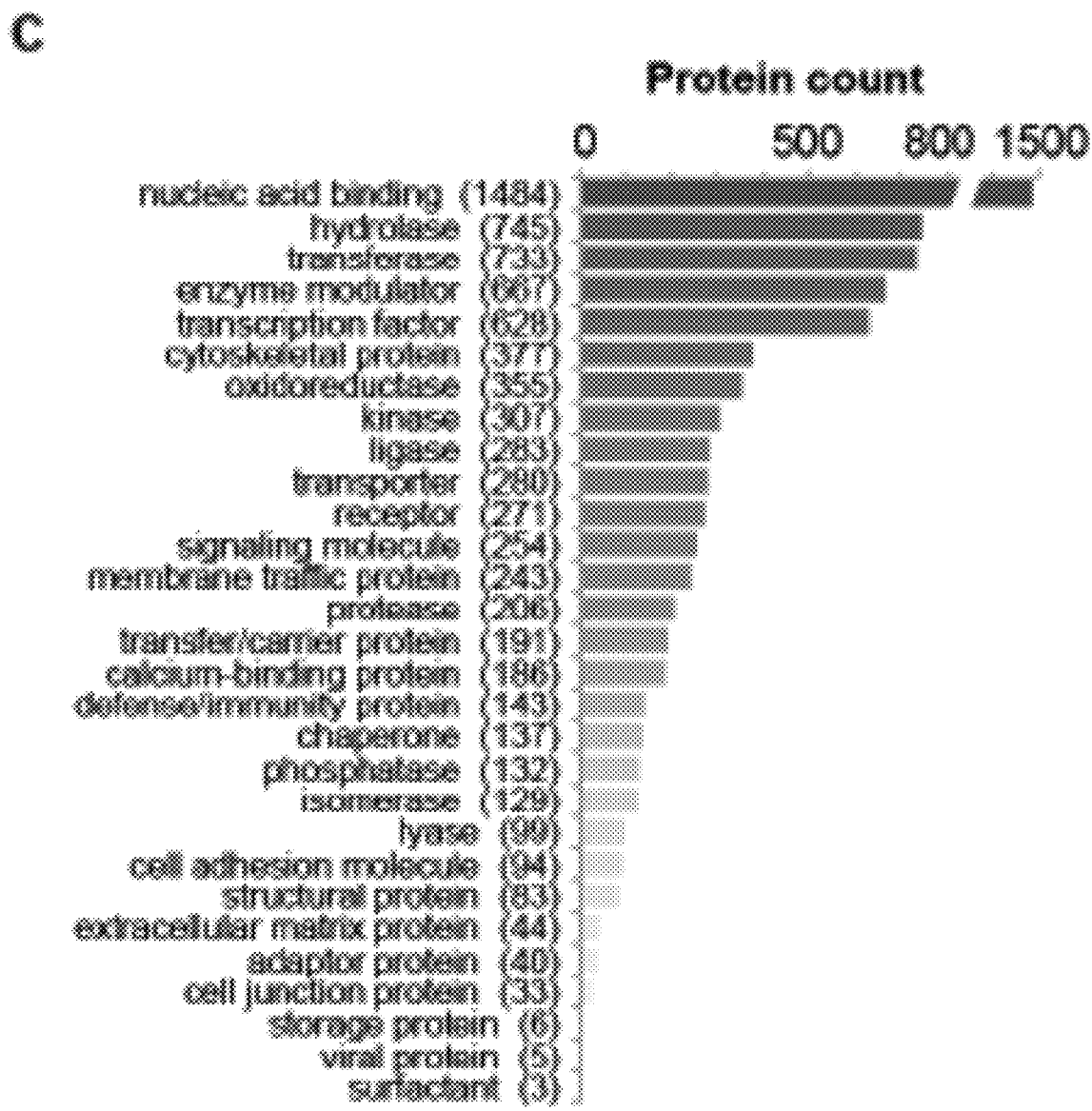

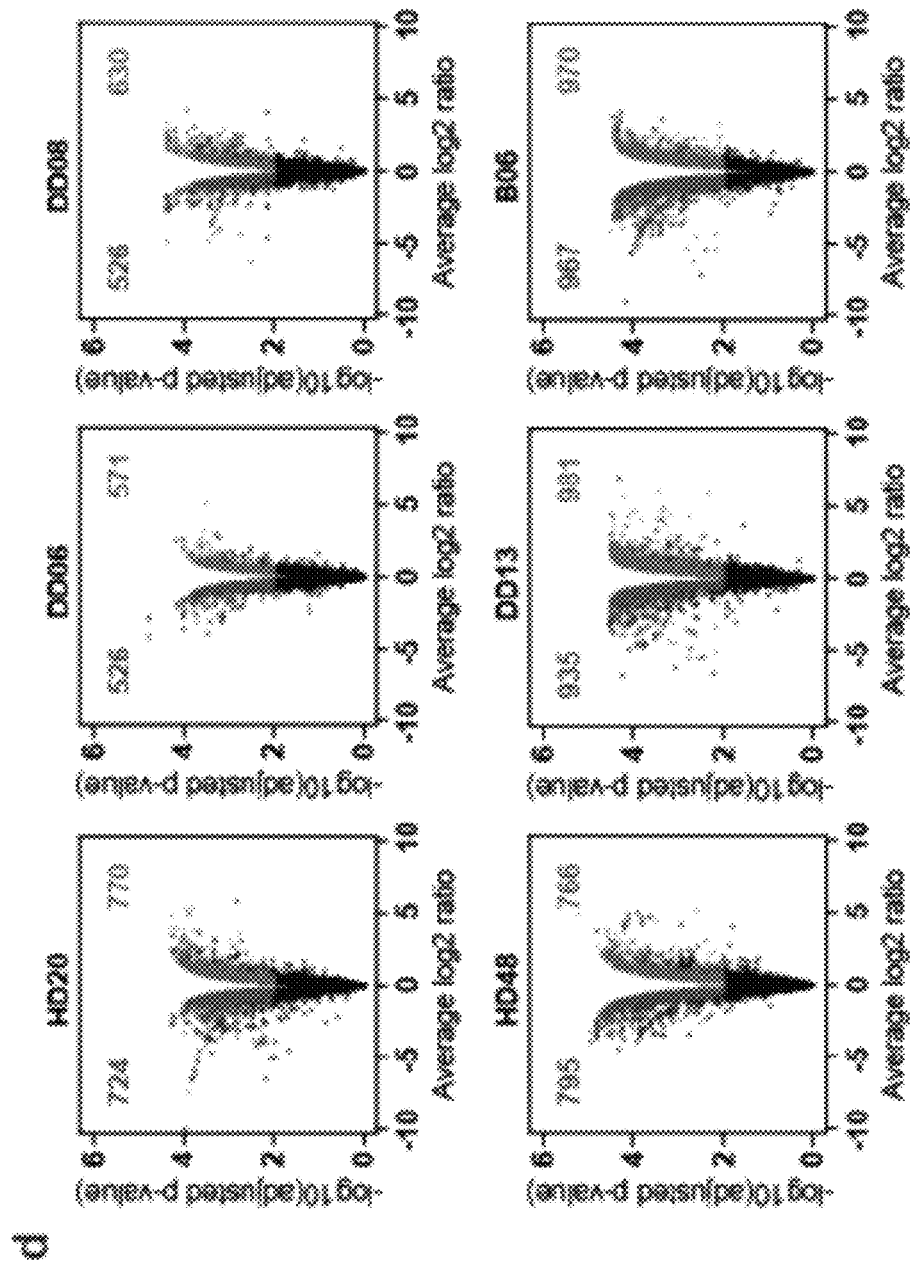
Figure 2 (contd.):

Figure 2 (contd.):
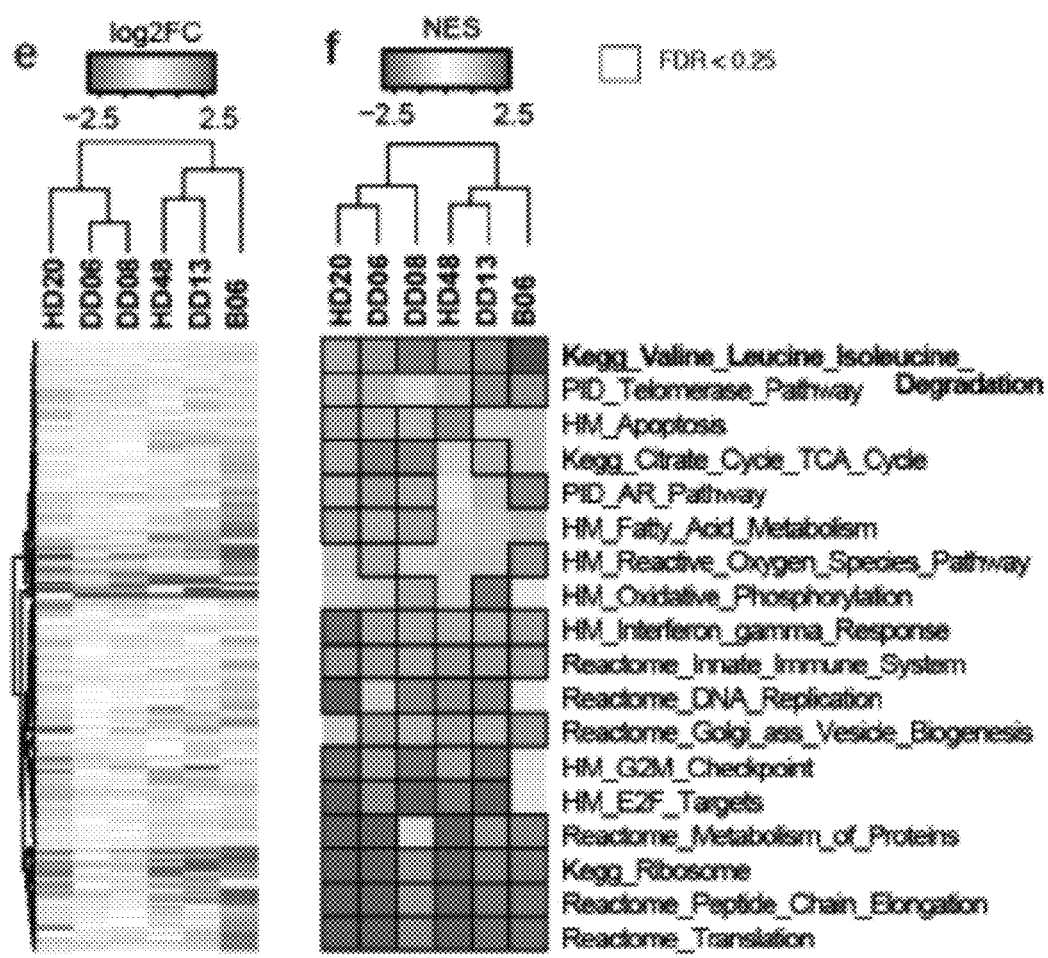

Figure 2 (contd.):
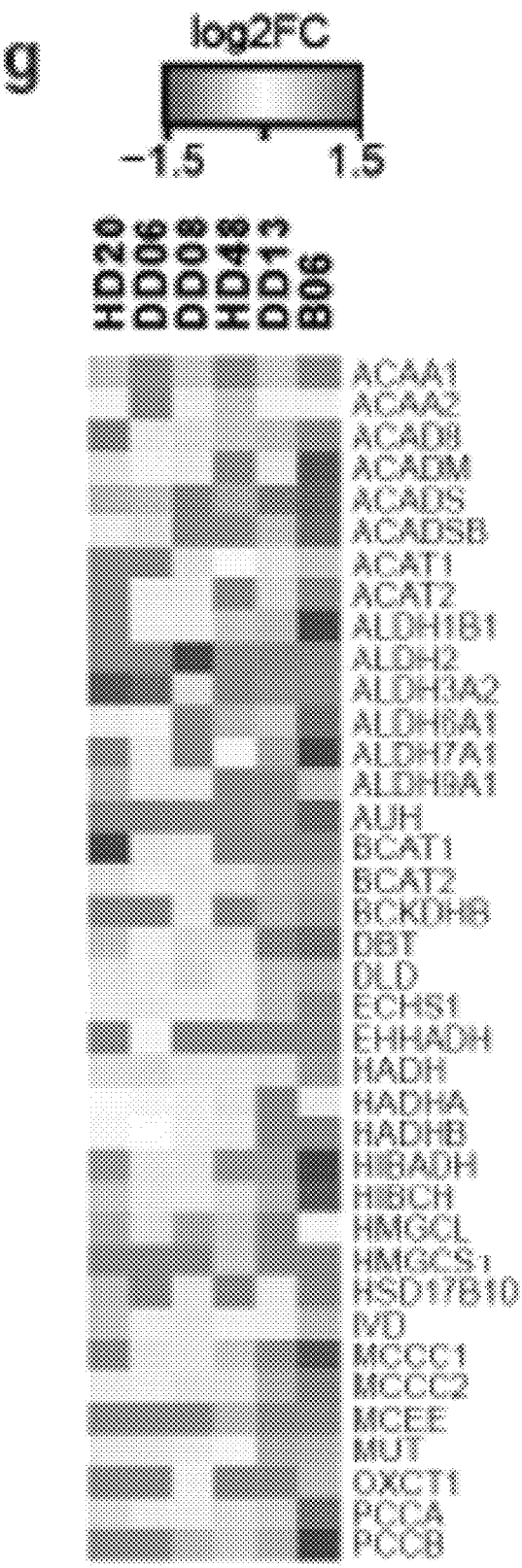

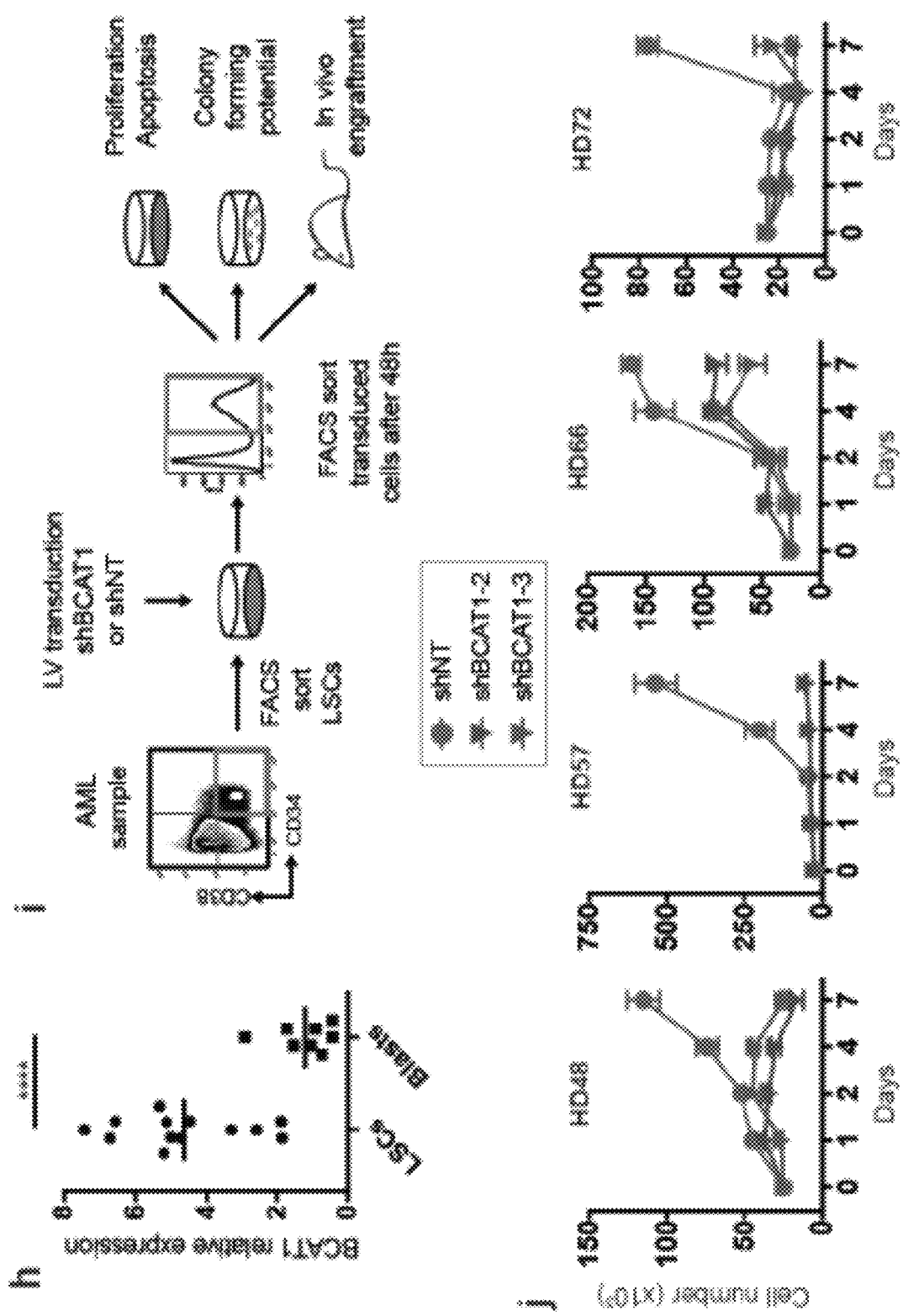
Figure 2 (contd.):

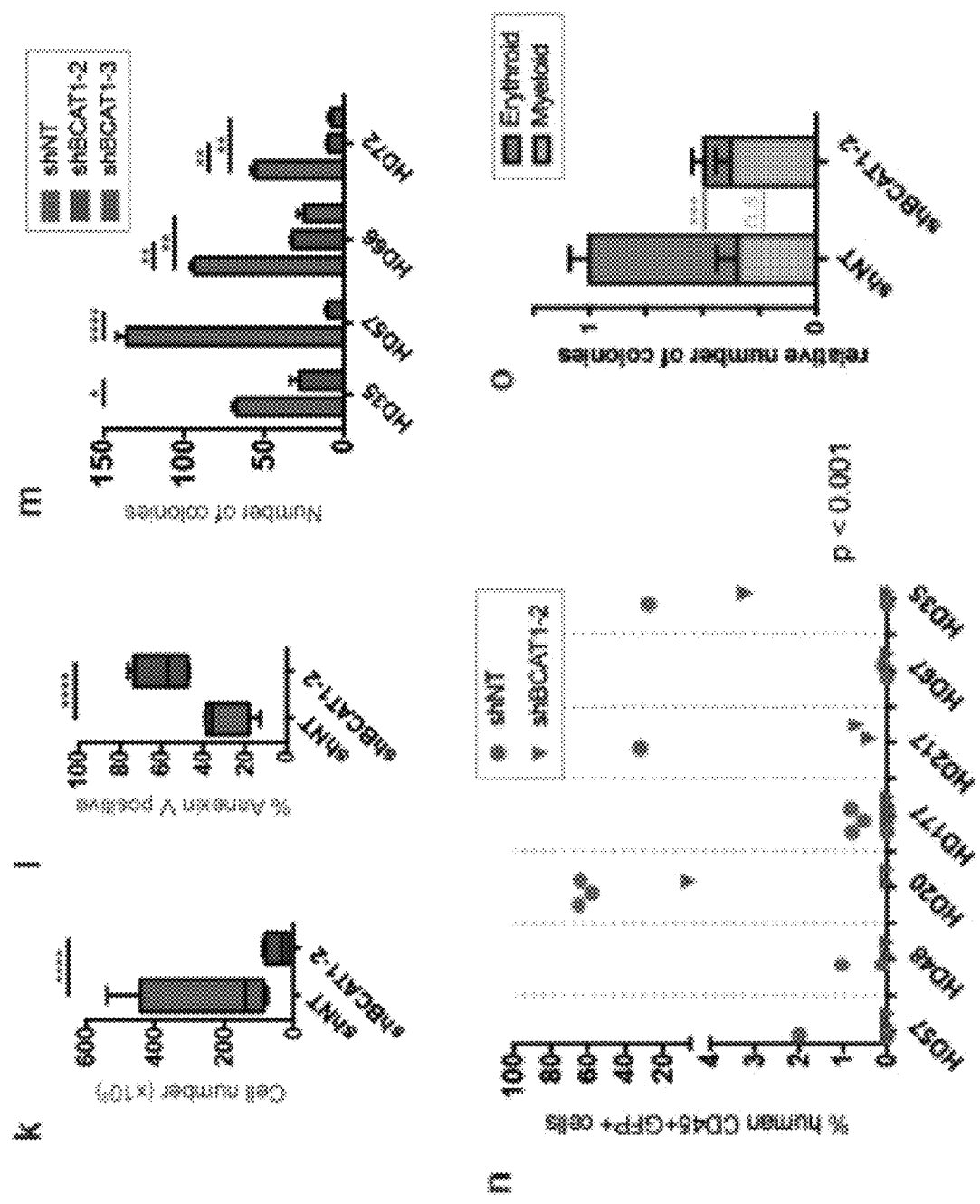
Figure 2 (contd.):

Figure 3 (contd.):
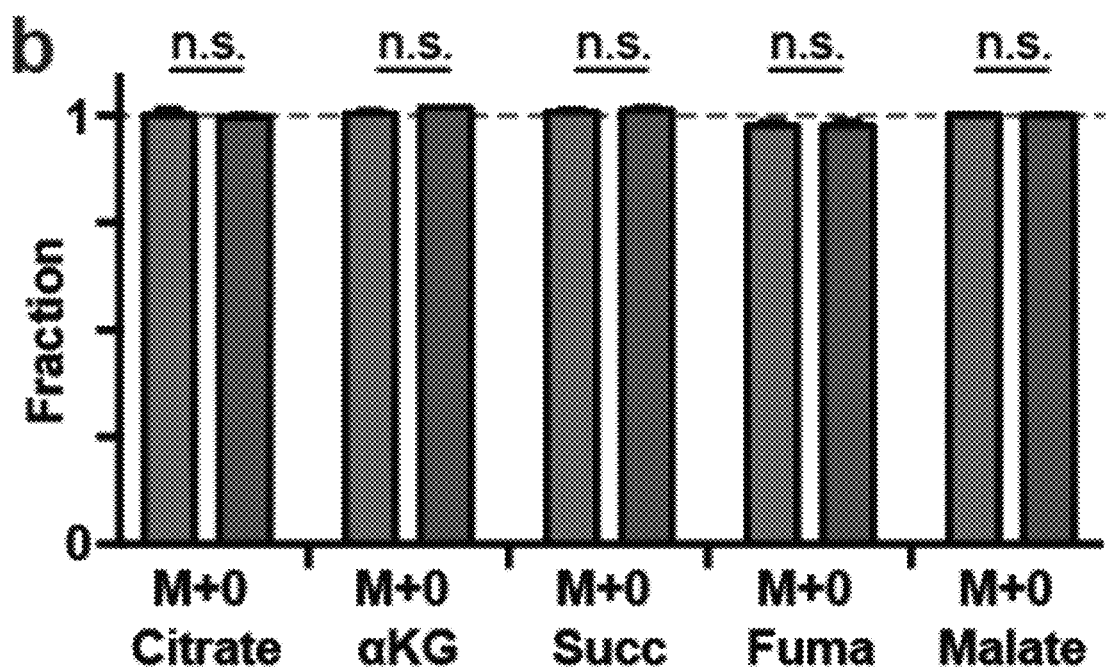
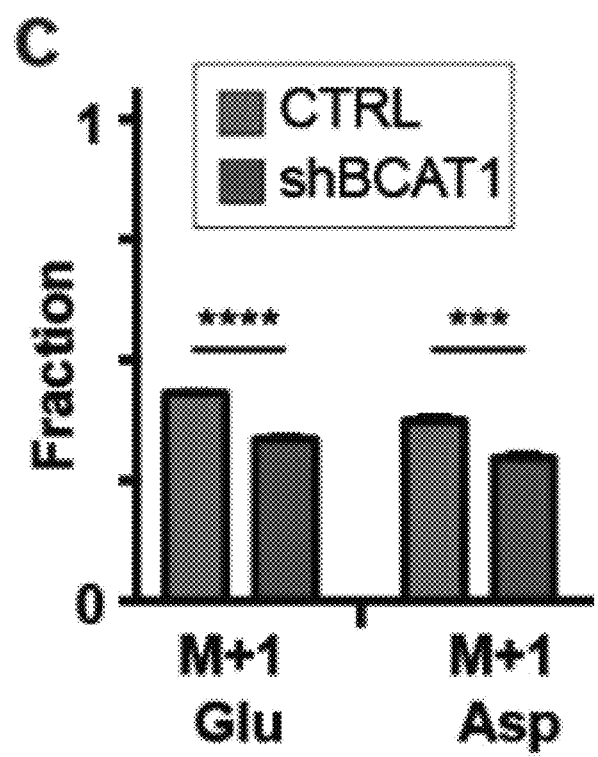

Figure 3 (contd.):
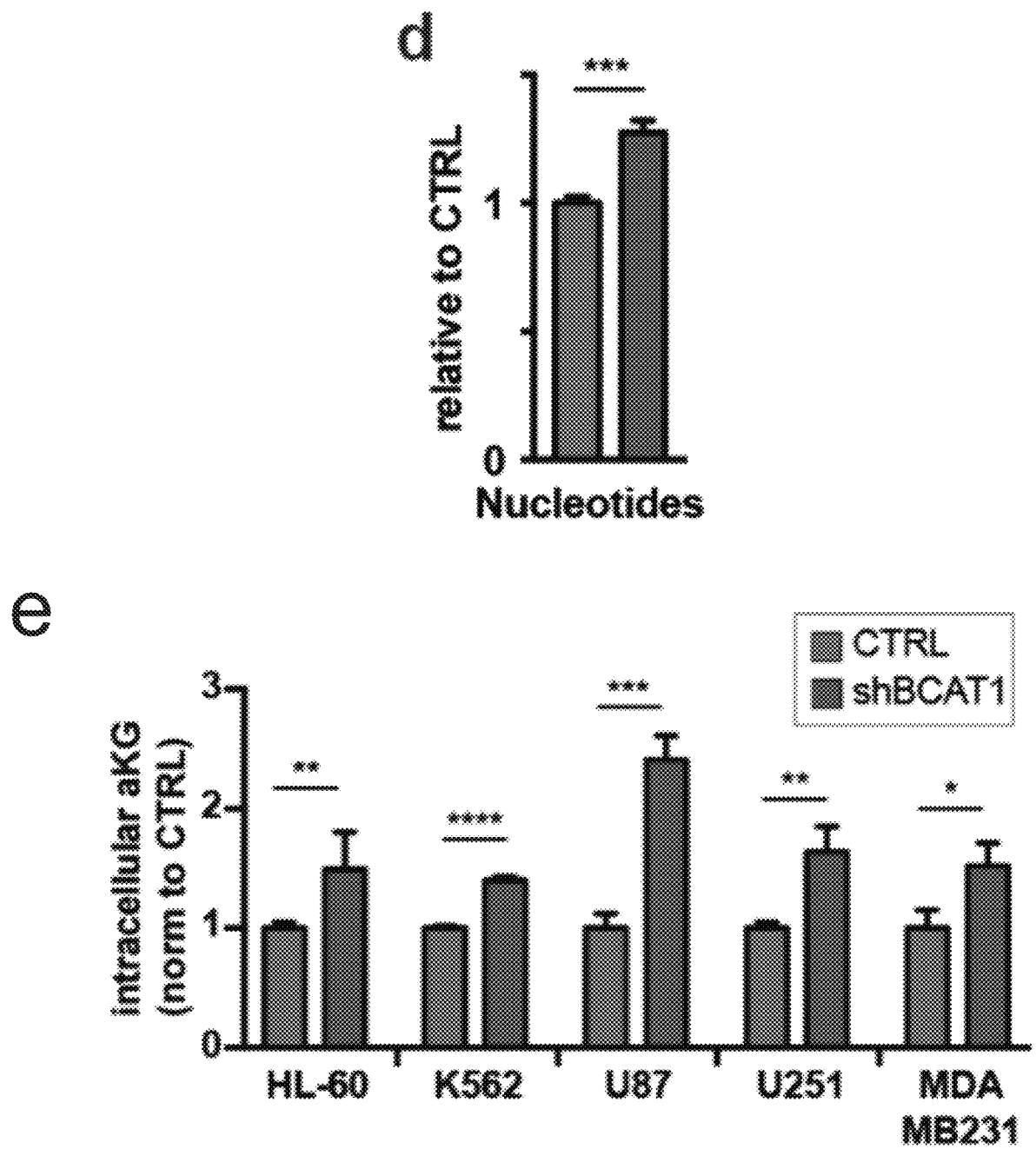

Figure 4 (contd.):
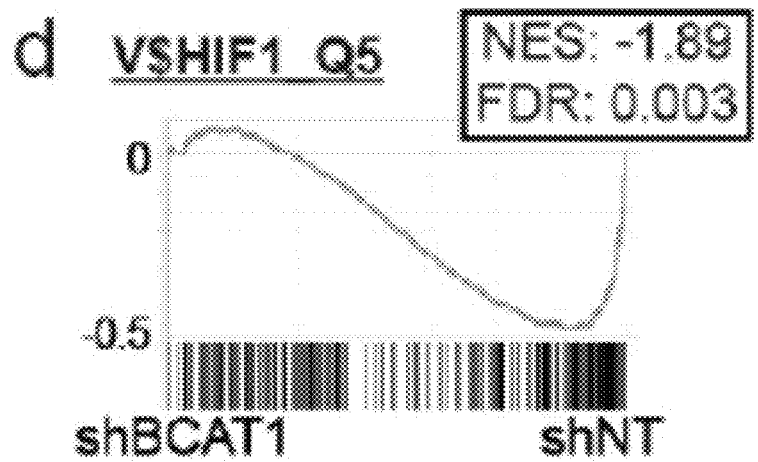
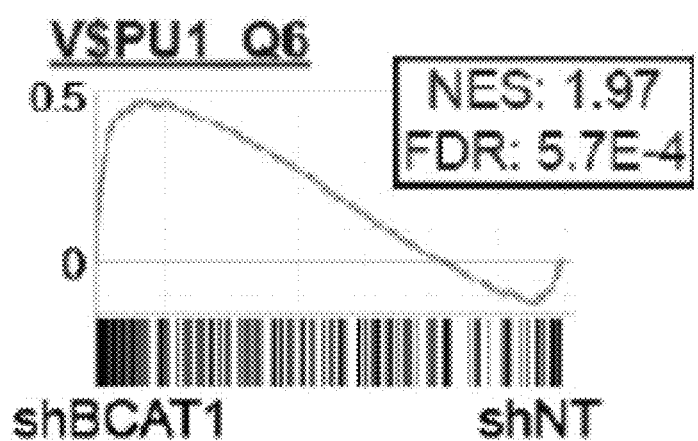
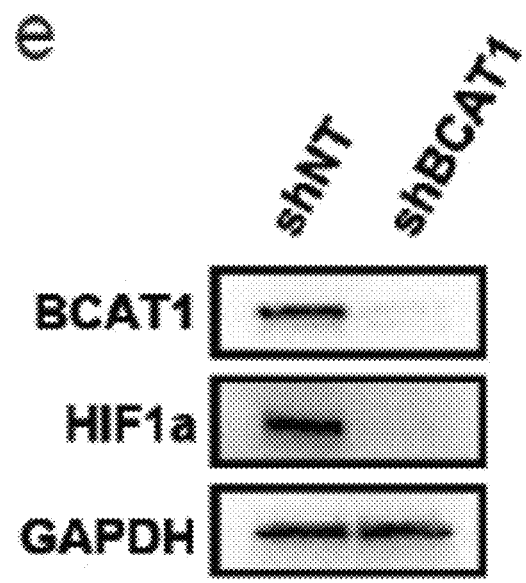

Figure 4 (contd.):
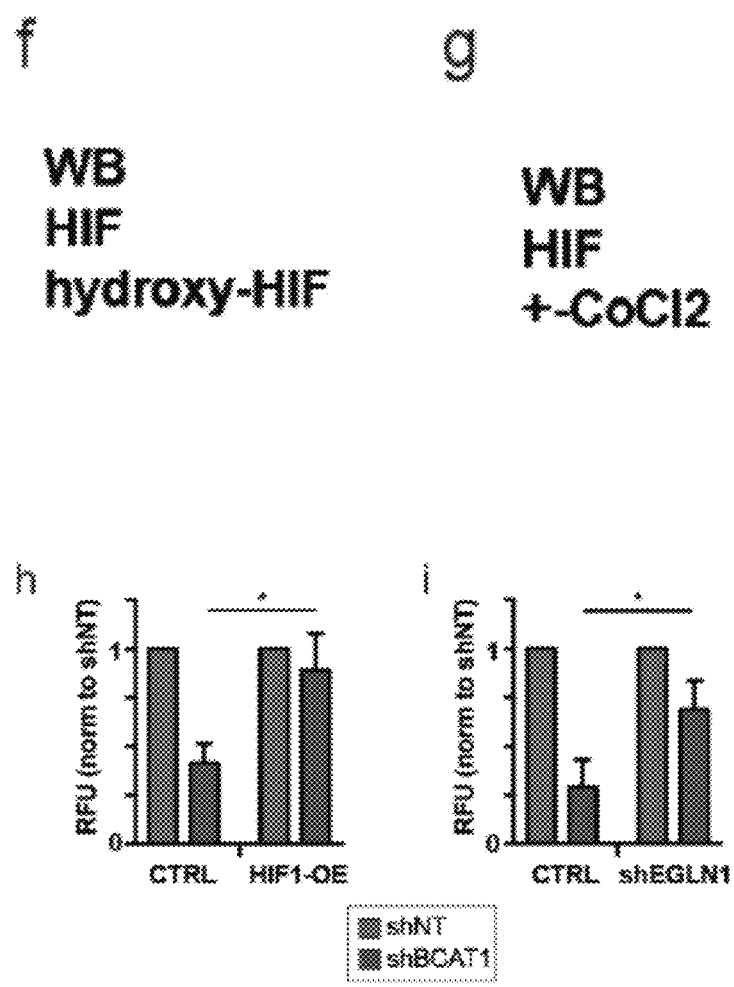

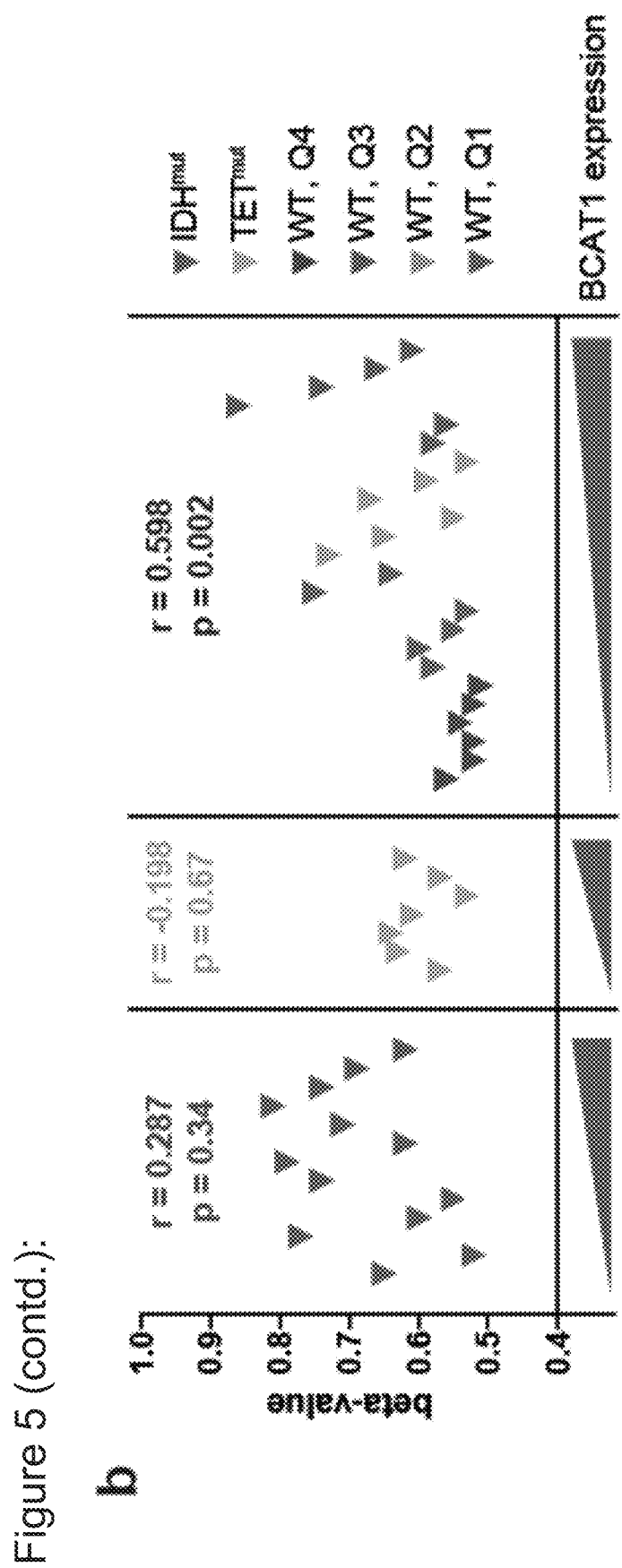
Figure 5 (contd.):

Figure 5 (contd.):
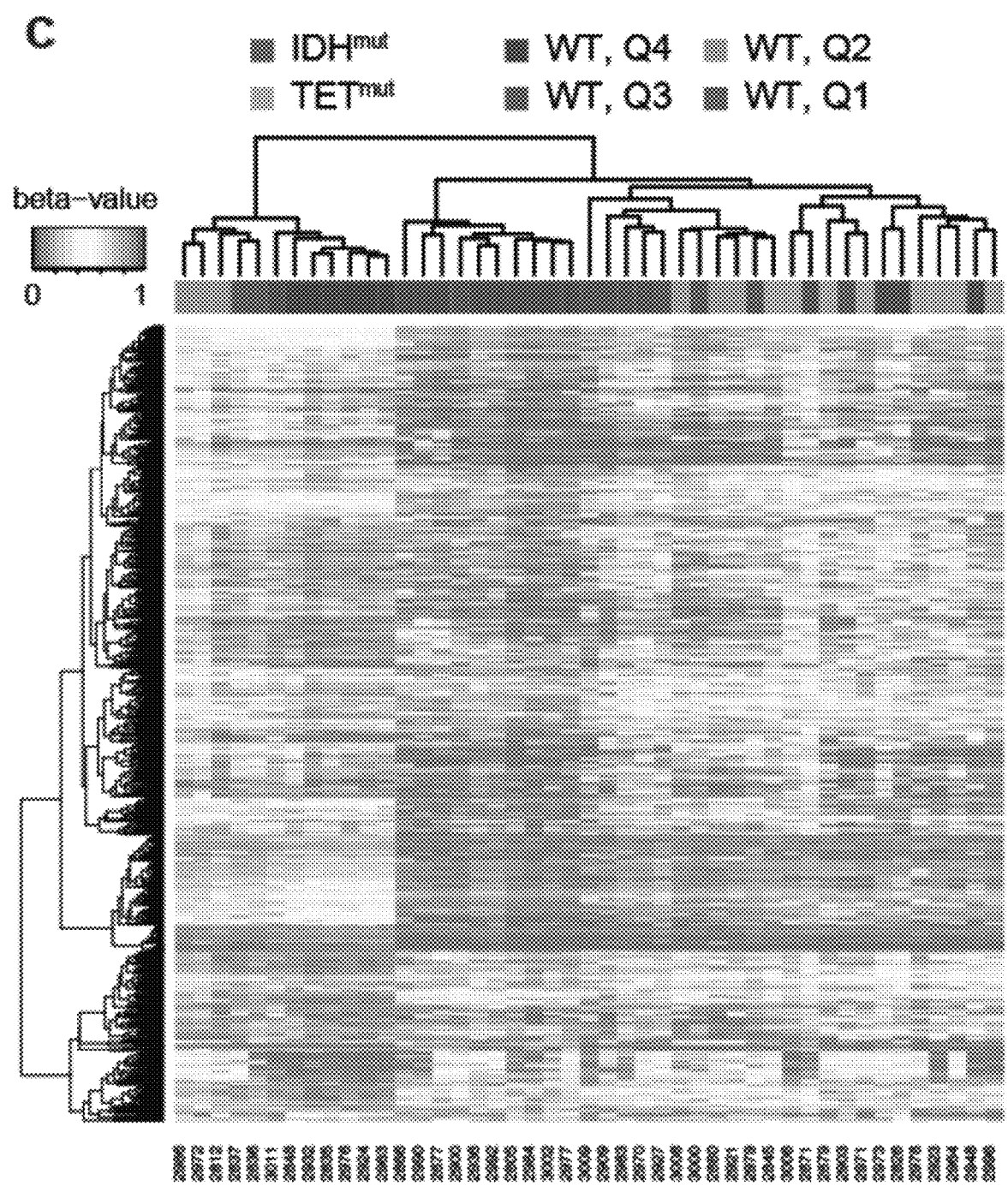

Figure 5 (contd.):
d
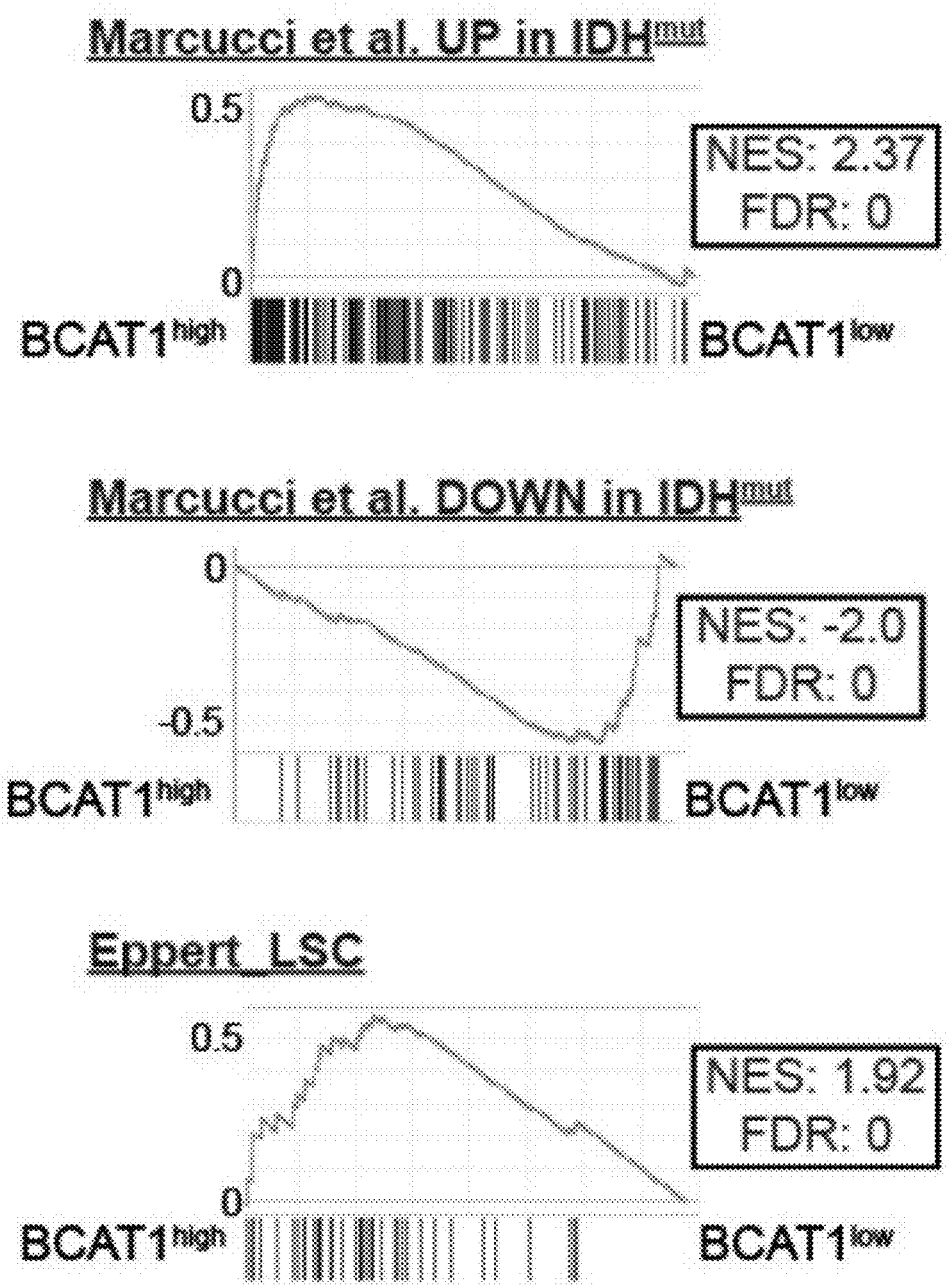

Figure 5 (contd.):
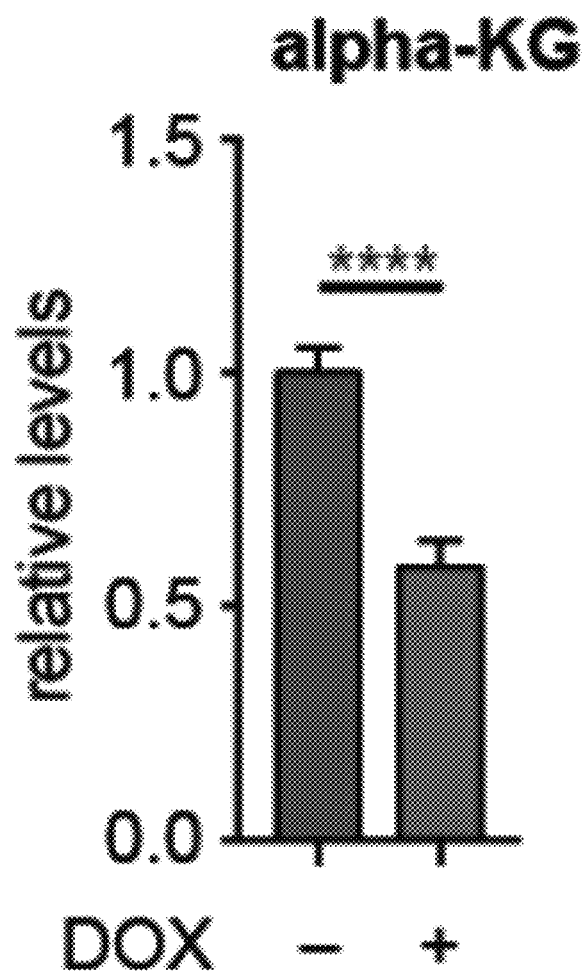

Figure 5 (contd.):
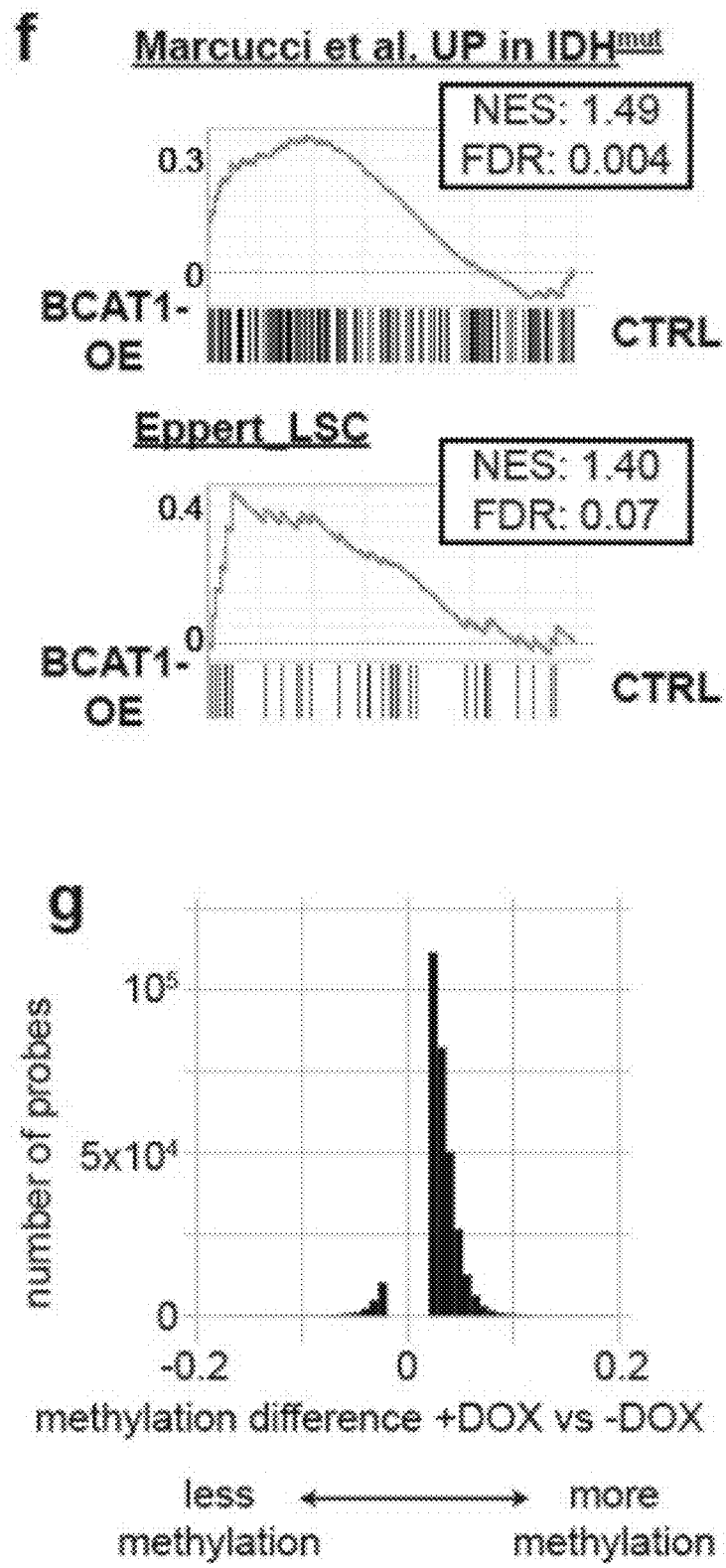

Figure 5 (contd.):
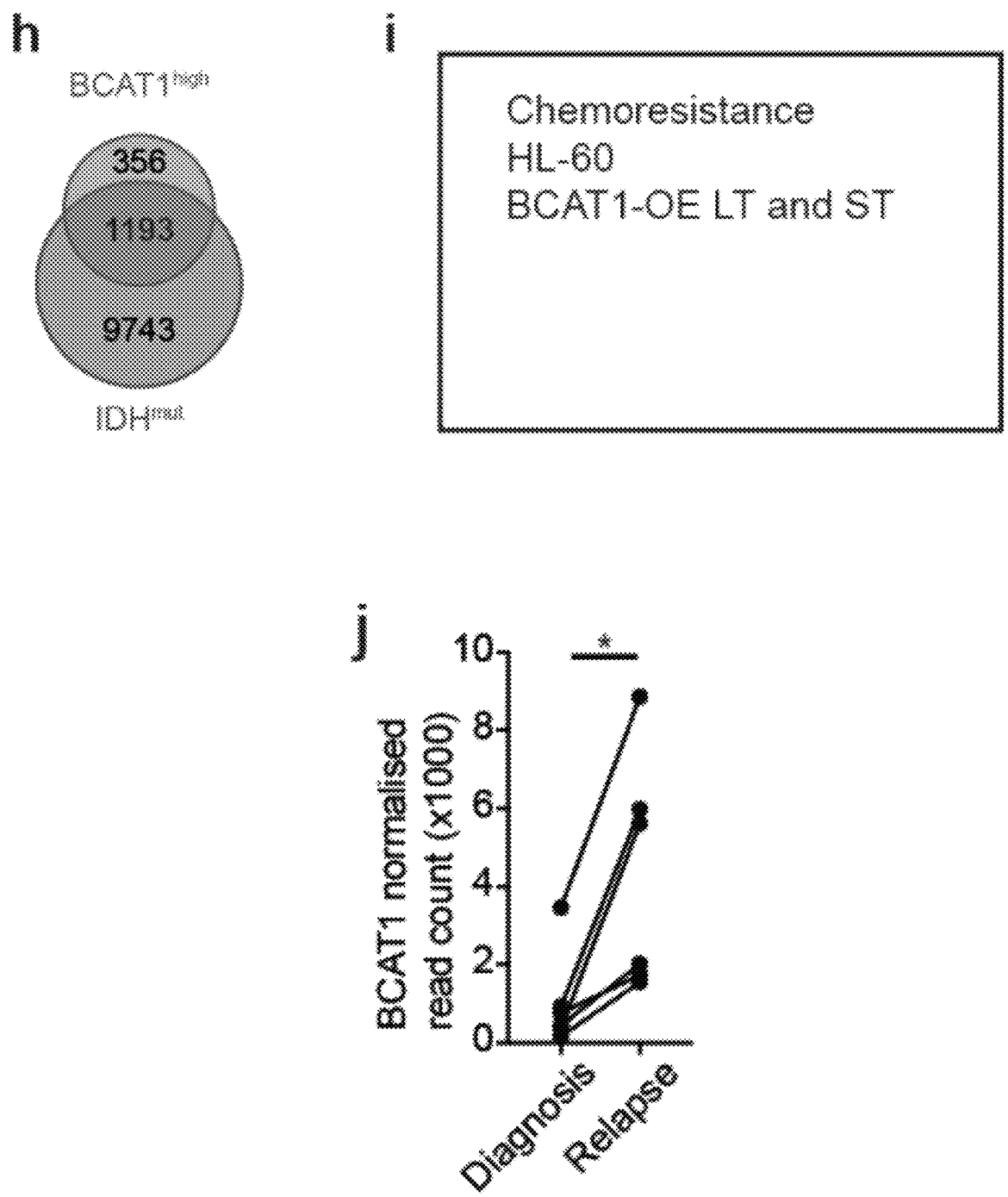

HR=1.494
p=0.0184

METHODS FOR SUB-TYPING AND TREATING CANCER

CROSS-REFERENCE TO RELATED APPLICATIONS

This application is a 371 national phase of International Patent Application No. PCT/EP2018/052410 filed 31 Jan. 2018, which claims priority to European Patent Application No. 17154260.8 filed 1 Feb. 2017, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WR-HS4-NP_sequence_listing.txt", which was created on Jul. 30, 2019, which is 3,651 bytes in size, and which is herein incorporated by reference in its entirety.

FIELD OF THE INVENTION

This invention relates to a novel approach for the identification and stratification of subtypes of cancer, particularly subtypes of cancer characterized by an increased expression of BCAT1, particularly Acute Myeloid Leukemia (AML). The invention furthermore relates to a novel approach with respect to the treatment of cancer, particularly Acute Myeloid Leukemia (AML).

BACKGROUND OF THE INVENTION

Personalized oncology has the potential to revolutionize the way cancer patients will be treated in the future. Different entities of cancer can be divided into subclasses based on molecular differences, including the specific activation of signaling pathways that often determine therapy response and clinical outcome. For various cancer entities including breast, lung and colon cancer, the identification of such subtypes and the possibility to stratify patients into cohorts has already been translated into clinical practice to treat patients in a subtype-specific manner.

Recently, the branched chain amino acid (BCAA) pathway and overexpression of (BCAA) transaminase (BCAT1) have been associated with aggressiveness in different cancer entities [1-4]. BCAT1 transfers the α-amino group from the essential BCAAs valine, leucine or isoleucine to α-ketoglutarate (αKG), which next to its role in the tricarboxylic acid (TCA) cycle is an essential co-factor for αKG-dependent dioxygenases such as EGLN1 or TET family of DNA demethylases (see FIG. 1).

In addition to its potential relevance in, for example, gliomas, ovarian cancer and nasopharyngeal carcinoma, BCAT1 has recently been listed as part of a gene signature in AML patients, where the signature showed distinct differences between low-risk and high-risk patients (Xie et al., Computational Biology and Chemistry, 67 (2017) 150-157).

However, the molecular mechanisms of how BCAT1 expression and the catabolic pathway it is involved in contribute to tumorigenesis remain unclear.

Thus, despite certain progress that has been made in the characterization and sub-typing of cancers, and the development of stratification and treatment approaches based on such developments, there is still a great need for the development of additional and/or refined methods for cancer patient stratification and the development of more efficient treatment schemes, particularly for the treatment of AML.

The solution to this problem, i.e. the sub-typing of AML patients based on a combination of BCAT1 expression status and of the genotype, and the identification of therapeutic approaches that modify and/or interfere with such status, are neither provided nor suggested by the prior art.

OBJECTS OF THE INVENTION

It was thus an object of the invention to provide novel approach for the identification and stratification of subtypes of AML. Additionally, it was an object of the invention to provide a novel approach with respect to the treatment of such AML subtypes of cancer. Such novel approaches would satisfy the great need for quick and reliable patient stratification to greatly improve prognostic evaluation and the introduction of novel cancer treatment approaches exploiting subtype-specific drug regimen.

SUMMARY OF THE INVENTION

Basis for the present invention is the identification that AML cell populations characterized by the presence of leukemia stem cells exhibit an increased BCAT1 expression level, resulting in an apparently decreased level of α-ketoglutarate present intracellularly, which could be increased by blocking BCAT1 expression. Since α-ketoglutarate is a co-factor of anti-tumorigenic and/or anti-proliferative pathways, such increase could potentially be of benefit to AML patient with increased BCAT1 expression. Surprisingly, it was found, that a certain subtype of AML patients, characterized by BCAT1$^{high}$ expression and IDH$^{wt}$TET$^{wt}$ benefit in particular from such increase. Without wishing to be bound by theory, it is assumed that BCAT-overexpression to a lesser degree (BCAT1$^{low}$) still maintains sufficient amounts of α-ketoglutarate, while in cells with mutations in IDH (IDH$^{mut}$), an alternative mechanism is present that inhibits the pathways α-ketoglutarate is involved in as a co-factor. This is particularly important, since high levels of BCAT1 are strongly correlated with shorter overall survival in IDH$^{wt}$TET$^{wt}$, but not in IDH$^{mut}$ AMLs.

Thus, in one aspect, the present invention relates to a compound that increases intracellular levels of α-ketoglutarate for use in the treatment of a patient suffering from AML, wherein said AML is characterized by BCAT1$^{high}$ expression and IDH$^{wt}$TET$^{wt}$.

In another aspect, the present invention relates to a method of treating a patient suffering from AML, wherein said AML is characterized by BCAT1$^{high}$ expression and IDH$^{wt}$ TET$^{wt}$, comprising the step of administering a compound that increases intracellular levels of α-ketoglutarate.

In another aspect, the present invention relates to an in vitro method for the characterization of the status of a patient suffering from AML, characterized by the steps of (i) measuring expression of BCAT1 and (ii) determining the genotype with respect to IDH and TET, in a sample comprising AML cells from said patient.

In another aspect, the present invention relates to an in vitro method of stratifying a patient suffering from AML, the method comprising the steps of:
  in vitro measuring expression of BCAT1 in AML tumor cells obtained from said patient;
  determining the status of said AML tumor cells with respect to IDH and TET; and stratifying said patient into a drug treatment cohort based on the status determined in steps (a) and (b);

wherein a patient characterized by BCAT1$^{high}$ expression and IDH$^{wt}$ TET$^{wt}$ may be treated by a compound that increases intracellular levels of α-ketoglutarate.

FIGURES

DETAILED DESCRIPTION OF THE INVENTION

The present invention may be understood more readily by reference to the following detailed description of the invention and the examples included therein.

Thus, in one aspect, the present invention relates to a compound that increases intracellular levels of α-ketoglutarate for use in the treatment of a patient suffering from AML, wherein said AML is characterized by BCAT1$^{high}$ expression and IDH$^{wt}$TET$^{wt}$.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In certain embodiments, the compound is a BCAT1 inhibitor.

In certain embodiments, said BCAT1 inhibitor is selected from: an antisense molecule, an siRNA molecule, an shRNA molecule, an inactive variant of BCAT1, and a small molecule inhibitor, particularly 1-(aminomethyl) cyclohexane acetic acid.

In the context of the present invention, the term "antisense molecule" refers to an oligonucleotide consisting of from 8 to 30 nucleotides, particularly from 12 to 25 nucleotides, more particularly from 13 to 20 nucleotides, wherein the sequence of said oligonucleotide corresponds to the antisense strand of the nucleic acid sequence coding for a protein of interest to be inhibited. In particular embodiments one or more nucleotide(s) in said oligonucleotide and/or one or more of the phosphate linkage groups are modified.

Figure 5:
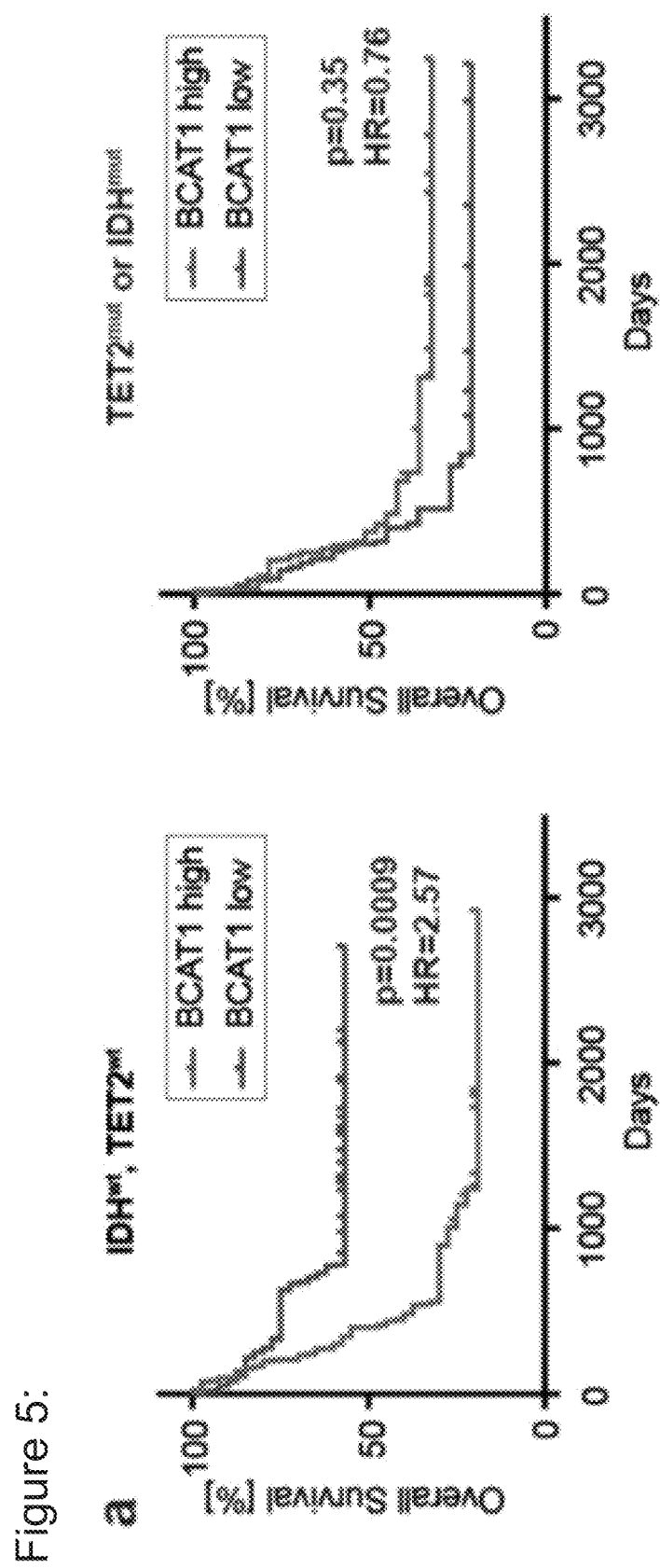
Figure 6:
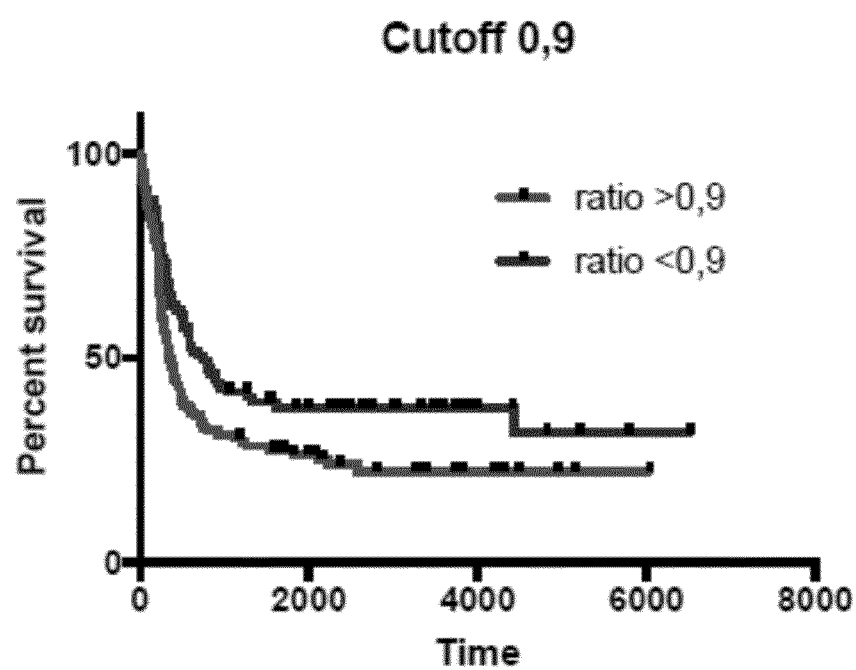
FIG. 6 shows the overall survival analysis of a BCAT1$^{high}$ patient population (BCAT1/ABL1 ratio>0.9) in comparison to a BCAT1$^{low}$ patient population (BCAT1/ABL1 ratio<0.9).

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altrose, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. Examples of the latter are: locked nucleic acid (LNA), 2',4' constrained ethyl nucleic acids (c-ET), 2'-0,4'-C-ethylene-bridged nucleic acid (ENA), polyalkylene oxide- (such as triethylene glycol (TEG)), 2'-fluoro-, 2'-deoxy-2'-fluoro-beta-D-arabinonucleic acid (FANA), 2'-0-methoxy- and 2'-O-methyl-modified nucleotides. FIG. 5 shows examples of a number of different modified nucleotides that may be used in the context of the present invention.

An "LNA" is a modified RNA nucleotide, wherein the ribose moiety is modified with an extra bridge connecting the 2' oxygen and 4' carbon (2'-4'ribonucleoside). The bridge locks the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and can be mixed or combined, respectively, with DNA or RNA residues in the oligonucleotide.

A "bridged nucleic acid" is modified RNA nucleotide, sometimes also referred to as constrained or inaccessible RNA molecule, which may contain a five-membered, six-membered or even a seven-membered bridged structure with a "fixed" C3'-endo sugar puckering. The bridge is synthetically incorporated at the 2',4'-position of the ribose to afford a 2',4'-BNA monomer. Specific examples are "ENA" nucleotides, wherein the bridge is an ethylene bridge. FIG. 5 shows a number of BNA nucleotides that may be used in the context of the present invention.

In a particular embodiment, one or more nucleotide(s) in said oligonucleotide are modified, wherein the modified nucleotide contains a modified phosphate group, particularly selected from a phosphorothioate and a methylphosphonate, particularly a phosphorothioate. In particular embodiments, all phosphate groups of the oligonucleotide are modified phosphate groups, particularly independently selected from phosphorothioates and methylphosphonates, particularly wherein all phosphate groups are phosphorothioates.

In a particular embodiment, one or more nucleotide(s) in said oligonucleotide are modified, wherein the modified nucleotide is an LNA, a c-ET, an ENA, a polyalkylene oxide-, a 2'-fluoro-, a 2'-O-methoxy-, a FANA and/or a 2'-O-methyl-modified nucleotide.

In particular embodiments, the modified nucleotide(s) is/are located within the stretch of 5 nucleotides at the 5'- and/or 3'-end of the oligonucleotide, particularly at the 5'- and the 3'-end of the oligonucleotide.

In particular embodiments, the oligonucleotides of the present invention comprise at least one modified nucleotide, particularly at least one LNA, c-ET and/or ENA, at the 5'- and/or 3'-end of the oligonucleotide. In a particular embodiment, the oligonucleotide comprises 1, 2, 3, or 4 LNAs or c-ETs or ENAs within the stretch of up to 5 nucleotides at the 5'-end, and 1, 2, 3, or 4 LNAs or c-ETs or ENAs within the stretch of up to 5 nucleotides at the 3'-end. In another particular embodiment, the oligonucleotide comprises 1, 2, 3, or 4 LNAs, c-ETs, or ENAs at the within the stretch of 5 nucleotides 5'-end or 3'-end, and a polyalkylene oxide such as TEG within the stretch of 5 nucleotides at the 3'- or 5'-end.

In particular embodiments, said oligonucleotide is a Gapmer comprising at least one LNA nucleotide within the stretch of 5 nucleotides at the 5'-end of said oligonucleotide, and at least one LNA nucleotide within the stretch of 5 nucleotides at the 3'-end of said oligonucleotide. In particular embodiments, said Gapmer comprises 2 or 3 LNA nucleotides within the stretch of 5 nucleotides at the 5'-end of said oligonucleotide, and 2 or 3 LNA nucleotides within the stretch of 5 nucleotides at the 3'-end of said oligonucleotide.

In the context of the present invention, the term "Gapmer" refers to a chimeric antisense oligonucleotide that contains a central block of deoxynucleotide monomers sufficiently long to induce RNase H cleavage. The central block of a Gapmer is flanked by blocks of 2'-O modified ribonucleotides or other artificially modified ribonucleotide monomers such as bridged nucleic acids (BNAs) that protect the internal block from nuclease degradation. In many earlier studies modified DNA analogs were investigated for their stability in biological fluids. In the majority of these experiments phosphorothioate DNA analogs were used. More recently, several types of artificial nucleotide monomers including BNA monomers have been investigated for their usefulness in the design of Gapmers. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects.

LNA Gapmers are powerful tools for loss of function studies of proteins, mRNA and lncRNAs. These single strand antisense oligonucleotides catalyze RNase H-dependent degradation of complementary RNA targets. LNA Gapmers are typically 12-20 nucleotides long enriched with LNA in the flanking regions and DNA in a LNA free central gap-hence the name Gapmer. The LNA-containing flanking regions confers nuclease resistance to the antisense oligo while at the same time increases target binding affinity regardless of the GC content. The central DNA "gap" activates RNase H cleavage of the target RNA upon binding.

Antisense molecules for the inhibition of BCAT1 have been described in the prior art (e.g. in EP 2 481 801 A1).

In the context of the present invention, the term "siRNA" refers to small (or short) interfering RNA molecules, which are a class of double-stranded RNA molecules having between 20 and 30, particularly between 20 and 25 base pairs in length. siRNA molecules interfere with the expression of the mRNA of genes with complementary nucleotide sequences and cause that mRNA to be cleaved after transcription resulting in no translation. siRNA constructs for the inhibition of BCAT1 have been described in the prior art (e.g. in WO 2012/100957) and are commercially available (e.g. from ThermoFisher Scientific, SigmaAldrich or Dharmacon).

In the context of the present invention, the term "shRNA" refers to small RNA-based molecules comprising sequences that form a small (or short) hairpin. Such shRNA sequence can be used to silence target gene expression via RNA interference (RNAi). Expression of shRNA in cells is typically accomplished by delivery of plasmids or through viral or bacterial vectors. shRNA constructs for the inhibition of BCAT1 have been described in the prior art (e.g. in Tönjes et al., Nature Medicine 19 (2013) 901-908) and are commercially available (e.g. from Origene, SigmaAldrich or Dharmacon).

In the context of the present invention, the term "inactive variant of BCAT1" refers to protein variants of BCAT1 that have a strongly reduced or completely abolished enzymatic activity of wild-type BCAT1, in particular variants resulting from modification at, or in vicinity to, the active site (lysine at amino acid position 202) or the core CXXC motif (amino acid positions 315 to 318 of BCAT1). Such modifications include the oxidation or labeling of hBCATm with sulfhydryl reagents. Inactive variants of BCAT1 have been described in the prior art (e.g. in Coles et al., Biochemistry 48 (2009):645-56).

Specific small-molecule inhibitors of BCAT1 are known in the art. For example, 1-(aminomethyl) cyclohexane acetic acid is described in WO 2012/100957. Additional small-molecule inhibitors being derivatives of 5-keto valeric acid are described in US 2016/368862, including the compounds 2 and 8:

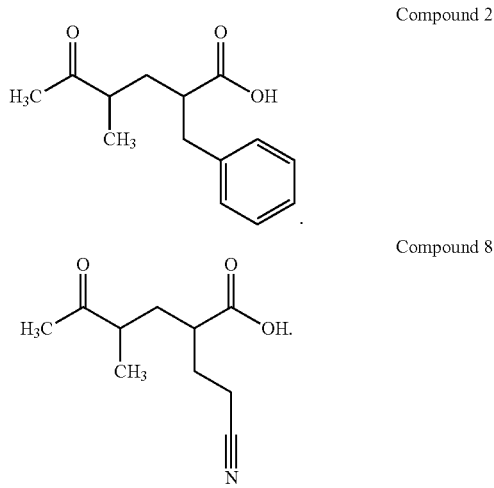

In certain other embodiments, said compound is selected from α-ketoglutaric acid, a mono- or dibasic salt of α-ketoglutaric acid, or a derivative of α-ketoglutaric acid having at least one of the carboxlic acid groups derivatized as ester or amide, particularly a mono-ester of α-ketoglutaric acid or a di-ester of α-ketoglutaric acid.

The compound α-ketoglutarate is known as a "molecule with pleiotropic activity", and its use in a number of therapeutic indications have been studied or at least suggested (for a review see Zdzisińnska et al. Arch Immunol Ther Exp (Warsz). 65 (2017) 21-36), In certain such embodiments, said compound is selected from 2-oxo-pentanedioic acid, 1-hexyl ester, 2-oxo-pentanedioic acid, 1-octyl ester, benzyl-α-ketoglutarate ester and 3-trifluoromethylbenzyl-α-ketoglutarate ester.

The synthesis of derivatives of α-ketoglutaric acid has been published (see, for example, Zengeya et al., Org Lett. 17 (2015):2326-9; MacKenzie et al., Mol Cell Biol. 27 (2007) 3282-3289)

In the context of the present invention, "characterized by $BCAT1^{high}$ expression and $IDH^{wt}TET^{wt}$" refers to BCAT1 expression above median in normal karyotype AML patients devoid of IDH and TET2 mutations.

In certain embodiments, said $BCAT1^{high}$ expression is determined by quantitative PCR.

In certain embodiments, said $BCAT1^{high}$ expression is determined in relation to the expression of a reference, particularly wherein said reference is ABL1, particularly wherein $BCAT1^{high}$ expression is characterized by a ratio of BCAT1/ABL1 of greater than 0.90. In particular embodiments, $BCAT1^{high}$ expression is characterized by a ratio of BCAT1/ABL1 of greater than 0.95, in particular greater than 1.00.

In another aspect, the present invention relates to a method of treating a patient suffering from AML, wherein said AML is characterized by BCAT1$^{high}$ expression and IDH$^{wt}$TET$^{wt}$, comprising the step of administering a compound that increases intracellular levels of α-ketoglutarate.

In certain embodiments, the compound is a BCAT1 inhibitor.

In certain embodiments, said BCAT1 inhibitor is selected from: an antisense molecule, an siRNA molecule, an shRNA molecule, an inactive variant of BCAT1, and a small molecule inhibitor, particularly 1-(aminomethyl) cyclohexaneacetic acid.

In certain other embodiments, said compound is selected from α-ketoglutaric acid, a mono- or dibasic salt of α-ketoglutaric acid, or a derivative of α-ketoglutaric acid having at least one of the carboxlic acid groups derivatized as ester or amide, particularly a mono-ester of α-ketoglutaric acid or a di-ester of α-ketoglutaric acid.

In certain such embodiments, said compound is selected from 2-oxo-pentanedioic acid, 1-hexyl ester and 2-oxo-pentanedioic acid, 1-octyl ester.

In certain embodiments, said BCAT1$^{high}$ expression is determined by quantitative PCR.

In certain such embodiments, said BCAT1$^{high}$ expression is determined in relation to the expression of a reference, particularly wherein said reference is ABL1, particularly wherein BCAT1$^{high}$ expression is characterized by a ratio of BCAT1/ABL1 of greater than 0.90. In particular embodiments, BCAT1$^{high}$ expression is characterized by a ratio of BCAT1/ABL1 of greater than 0.95, in particular greater than 1.00.

In another aspect, the present invention relates to an in vitro method for the characterization of the status of a patient suffering from AML, characterized by the steps of (i) measuring expression of BCAT1 and (ii) determining the genotype with respect to IDH and TET, in a sample comprising AML cells from said patient.

In another aspect, the present invention relates to an in vitro method of stratifying a patient suffering from AML, the method comprising the steps of:

in vitro measuring expression of BCAT1 in AML tumor cells obtained from said patient;
determining the status of said AML tumor cells with respect to IDH and TET; and stratifying said patient into a drug treatment cohort based on the status determined in steps (a) and (b);
wherein a patient characterized by BCAT1$^{high}$ expression and IDH$^{wt}$TET$^{wt}$ may be treated by a compound that increases intracellular levels of α-ketoglutarate.

In certain embodiments, said BCAT1$^{high}$ expression is determined by quantitative PCR.

In certain embodiments, said BCAT1$^{high}$ expression is determined in relation to the expression of a reference, particularly wherein said reference is ABL1, particularly wherein BCAT1$^{high}$ expression is characterized by a ratio of BCAT1/ABL1 of greater than 0.90. In particular embodiments, BCAT1$^{high}$ expression is characterized by a ratio of BCAT1/ABL1 of greater than 0.95, in particular greater than 1.00.

In certain embodiments, said tumor cells are cells from a tumor sample.

In certain embodiments, said sample is obtained from a mammal, particularly a human.

In the context of the present invention, the term "stratifying" or "stratification" relates to the identification of a group of patients with shared "biological" characteristics by using molecular and biochemical diagnostic testing to select the optimal management for the patients.

In certain embodiments, said tumor cells are obtained by purifying tumor cells from a tumor sample from said patient, particularly wherein the purification comprises flow sorting or laser capture microdissection.

In a particular embodiment, the patient sample is selected from blood, serum, and plasma. In a particular embodiment, the patient sample is a collection of circulating tumor cells (CTCs), particularly isolated from the blood of a patient. In particular embodiments, the CTCs are isolated by apheresis.

In certain embodiments, said tumor cells are (i) isolated from the blood of said patient; or (ii) isolated from a tumor sample, which is a tumor biopsy.

EXAMPLES

Example 1

Branched Chain Amino Acid Catabolism is Overactivated in Leukemic Stem Cells Mimicking Epigenetic Changes Induced By Mutations in IDH and TET2

In an unbiased high-resolution proteomics analysis of leukemic stem cell (LSC+) and non-LSC (LSC−) populations of human Acute Myeloid Leukemia (AML) samples, we identified the BCAA pathway and BCAT1 as commonly overexpressed in LSCs. Knockdown (KD) of BCAT1 in leukemic cells caused an accumulation of αKG resulting in HIF1 protein degradation mediated by EGLN1 activity. BCAT1-KD cells display decreased leukaemia-initiating potential and a growth and survival defect rescued by overexpression of HIF1 or knockdown of EGLN1. In contrast, overexpression (OE) of BCAT1 in leukemic cells decreases intracellular αKG levels and results in DNA hypermethylation mediated by decreased αKG dependent DNA demeythylase activity. BCAT1$^{high}$ AML samples displayed a DNA hypermethylation phenotype similar to IDH$^{mut}$ cases in which αKG is inhibited by the oncometabolite 2-HG. High levels of BCAT1 is strongly correlated with shorter overall survival in IDH$^{wt}$TET$^{wt}$, but not IDH$^{mut}$AMLs. Gene sets characteristic for IDH$^{mut}$ AMLs and LSCs were enriched both in IDH$^{wt}$TET$^{wt}$BCAT1$^{high}$ patients and in BCAT1-OE leukemic cells. In summary, BCAT1 influences the cellular methylome by controlling intracellular αKG and the associated activity of αKG-dependent dioxygenases. High BCAT1 expression partially mimics IDH mutations in AML and BCAT1-derived αKG functions as a naturally occurring tumour suppressor metabolite. Therapeutic strategies to increase αKG by inhibition of BCAT1 in order to compromise LSC function, may lead to lower relapse rates and improved survival of AML patients.

Figure 1:
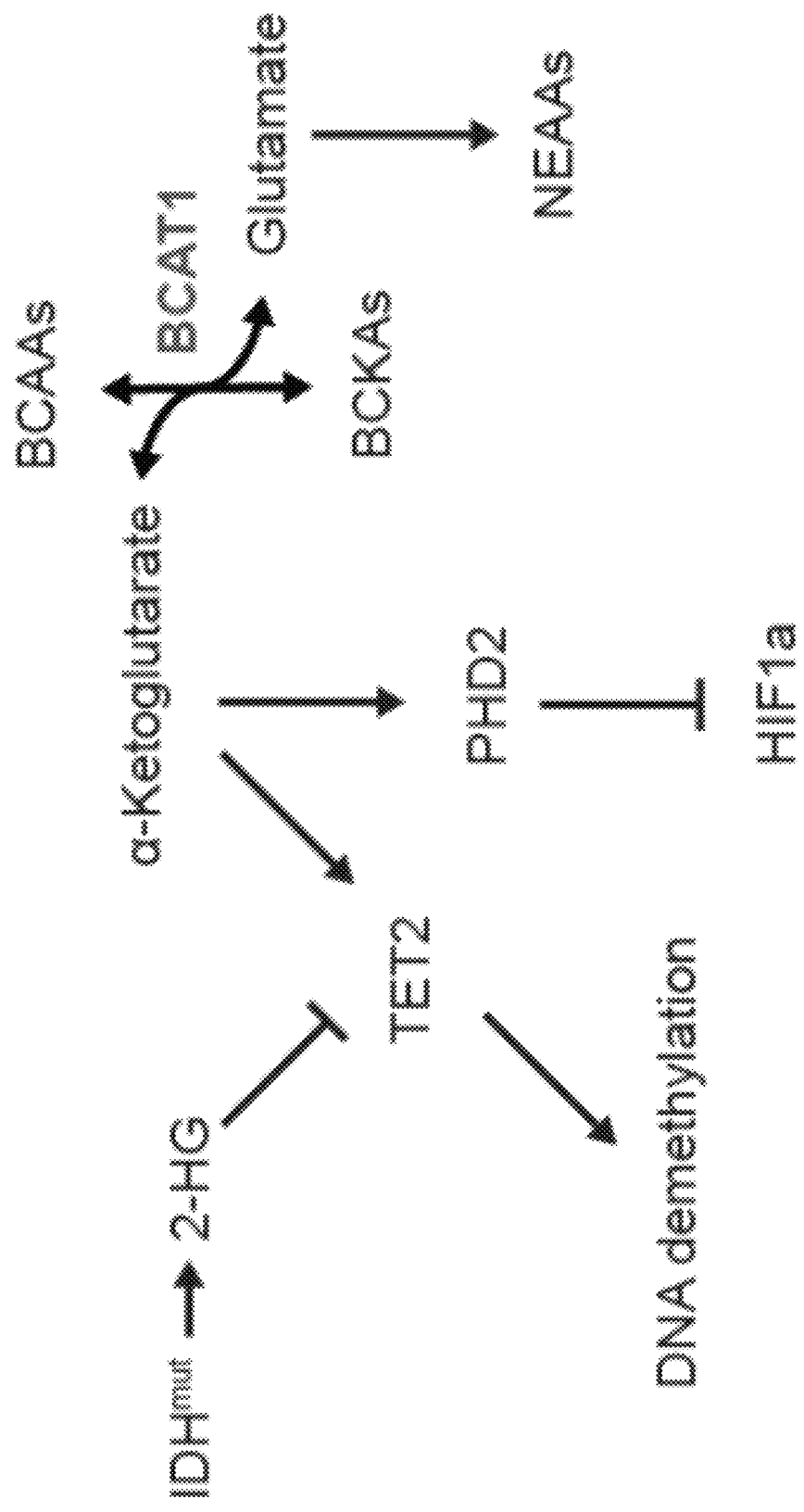
FIG. 1 shows a schematic view of certain roles and functions of BCAT1 and of α-ketoglutarate in branched chain amino acid catabolism, as well as of α-ketoglutarate as co-factor for α-ketoglutarate-dependent dioxygenases such as EGLN1 or for the TET family of DNA demethylases.
Figure 2:
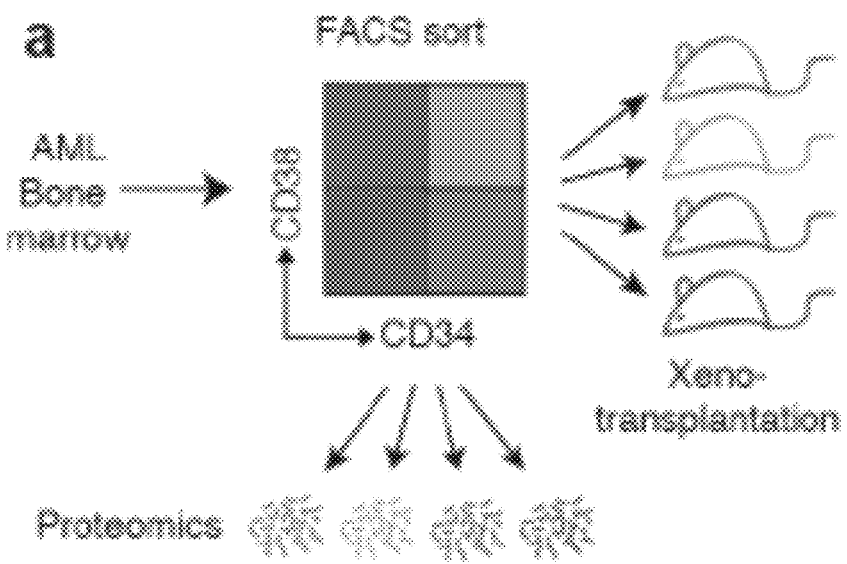
FIGS. 2 to 5 show the results of the experiments described in Example 1. Further explanations to the Figures and their individual sub-parts can be found in the text of Example 1.

Primary AML samples of two different subgroups (FLT3$^{ITD}$/NPM1$^{mut}$ and FLT3$^{wt}$/NPM1$^{wt}$) were fractionated according to CD34 and CD38 surface expression and functionally tested for the presence of leukaemia stem cells (LSCs) by xenotransplantation into NOD.Prkdc$^{scid}$.Il2rg$^{null}$ (NSG) mice (FIG. 2a). Consistent with previous reports we found LSC activity mainly in the CD34+fractions[5-7], however, LSCs were detected in all fractions with the exception of CD34-CD38+(FIG. 2b), underscoring the importance of functional assays to define LSC activity. 18 fractions (10 LSC+and 8 LSC−) of 6 primary AML samples were subjected to in-depth quantitative multiplex proteomic analysis employing tandem mass tag (TMT) labelling and high-resolution mass spectrometry (FIG. 2 a, b). More than 7,200 proteins, including low abundance proteins such as transcription factors, receptors and cell adhesion molecules, were detected (FIG. 2c). To derive LSC protein signatures for individual AML cases, we first calculated differentially expressed proteins between CD34+CD38−LSC+ and CD34−CD38+ LSC− fractions (padj<0.001) and subsequently selected those proteins that were over-represented also in the remaining LSC+ or LSC− fraction, respectively, of the individual patient. We detected between 1097 and 1937 differentially expressed proteins for each sample (FIG. 2d) and, interestingly, these proteins clustered per AML subtype, suggesting subtype-specific differences also in the LSC containing compartment (FIG. 2e). Gene Set Enrichment analyses (GSEA) on the protein data revealed, among others, a significant enrichment of DNA replication and protein translation in LSC− fractions, in line with their more proliferative state[8] (FIG. 2f). The most highly enriched process in LSC+ fractions across all patients was the degradation of the branched chain amino acids (BCAA) valine, leucine and isoleucine. The BCAA pathway has recently been associated with tumour aggressiveness in different entities, including IDH$^{wt}$ gliomas[1], hepatocellular[3] and ovarian cancer[2]. In agreement with the GSEA results, the vast majority of enzymes within this pathway were overexpressed in LSCs (FIG. 2g). We focused on BCAT1 that catalyses the first step of BCAA degradation and confirmed its higher expression levels in LSCs in an extended set of primary AML samples (FIG. 2h). To assess the functional role of BCAT1, we performed lentiviral knockdown (KD) experiments with functionally validated LSC+ populations (FIG. 2i). While control transduced cells proliferated normally, BCAT1-KD significantly impaired proliferation and survival (FIG. 2j-l). BCAT1-KD AML LSCs of all tested patients produced significantly less colonies in Colony Forming Unit (CFU) assays (FIG. 2m) and showed strongly reduced leukemia-initiating potential when transplanted into NSG mice (FIG. 2n). BCAT1-KD in healthy CD34+ cord blood impaired erythroid colony formation only, while the potential to from myeloid colonies was unaffected (FIG. 2O), in line with a recent report that interference with glutamine/glutamate metabolism impairs erythroid differentiation[9] (see below). Together, we found BCAT1 overexpressed in the AML LSC+compartment, constituting a critical enzyme for proliferation, survival and stem cell maintenance in primary AMLs.

Figure 3:
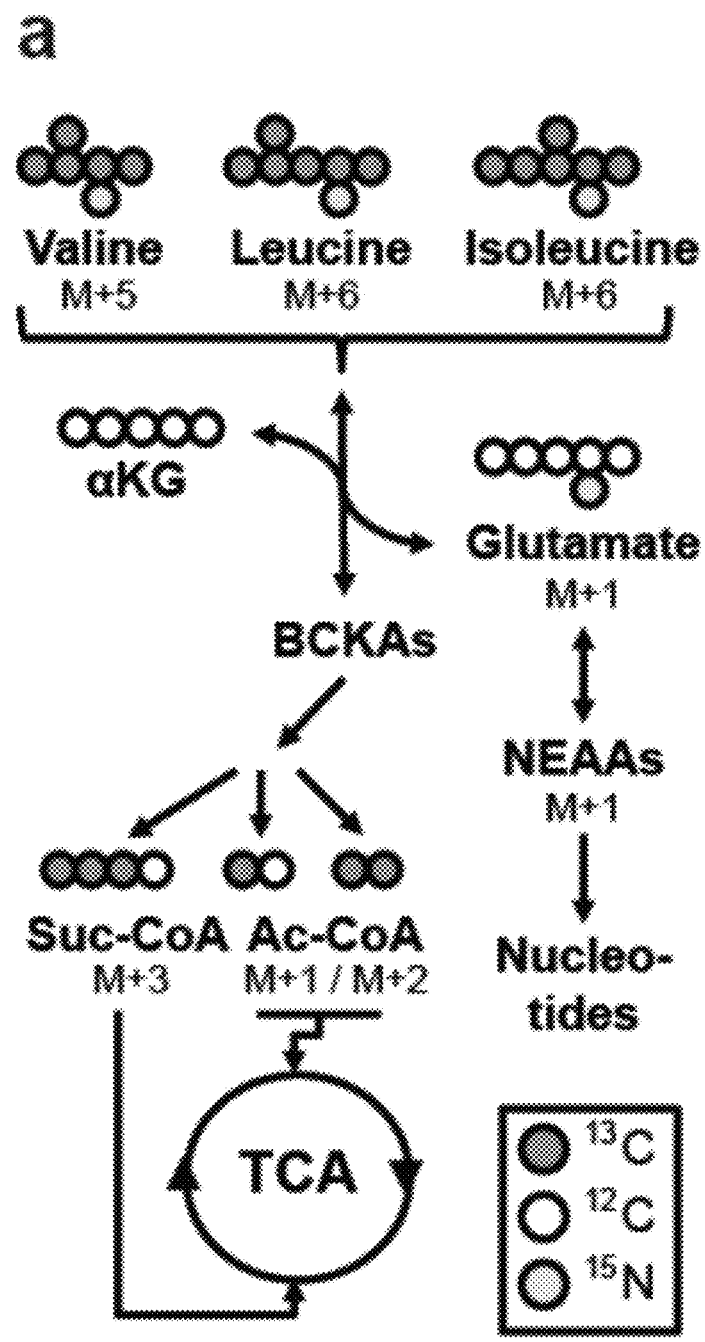

Cytosolic BCAT1 transfers an α-amino group from BCAAs to α-ketoglutarate (αKG) yielding glutamate and the respective branched-chain α-ketoacid (BCKA)[10]. After this transamination, BCKAs are thought to be further catabolised to acetyl- and succinyl-CoA, which enter the tricarboxylic acid (TCA) cycle (FIG. 3a). However, in tracing experiments with isotope-labelled BCAAs using the HL-60 AML cell line no labelled carbons were detected in the TCA intermediates, suggesting an alternative metabolic route of BCKA in these cells (FIG. 3b). Similar observations have been recently reported for other cell types, suggesting a general feature of the BCAA degradation pathway[4,11]. BCAA nitrogen transamination contributes to nonessential amino acid biosynthesis and downstream of this pathway, the nitrogen can be incorporated into nucleotides (ref). Consistently, we found incorporation of $^{15}$N into glutamate and aspartate (FIG. 3c), and other non-essential amino acids (NEAA) (data not shown). Upon knockdown of BCAT1 the fraction of $^{15}$N-labelled NEAAs was significantly decreased (FIG. 3c). Unexpectedly, global nucleotide levels were not decreased (but elevated) in BCAT1-KD cells (FIG. 3d), suggesting a very limited contribution of BCAA-derived nitrogen to nucleotide production in these cells. Consequently, supplementation of nucleotides was not sufficient to rescue the proliferation defect of BCAT1-KD cells. Given that BCAT1 utilizes αKG as substrate for the transamination we next hypothesized that BCAT1 activity contributes to the regulation of intracellular αKG levels. Indeed, upon BCAT1-KD the intracellular levels of αKG significantly increased in HL-60 cells (FIG. 3e). We validated this finding in K562 (leukaemia), U87 and U251 (glioma) and MDA MB-231 (breast cancer) cell lines, consistently showing significantly higher levels of αKG (between 1.4 and 2.4-fold) upon knockdown of BCAT1 (FIG. 3e). In summary, these experiments identify BCAT1 as a critical regulator of intracellular αKG levels in a broad range of different tumour types. Beyond its role in intermediary metabolism, αKG functions also as a signalling molecule being an essential co-substrate for cellular dioxygenases[12], which have activities potentially susceptible to small changes in αKG levels[13]. Among others, these enzymes include the Egl-9 Family Hypoxia Inducible Factor 1 (EGLN1) that hydroxylates and targets HIFs for proteasomal degradation[14] and the TET family of DNA demethylases[15].

Figure 4:
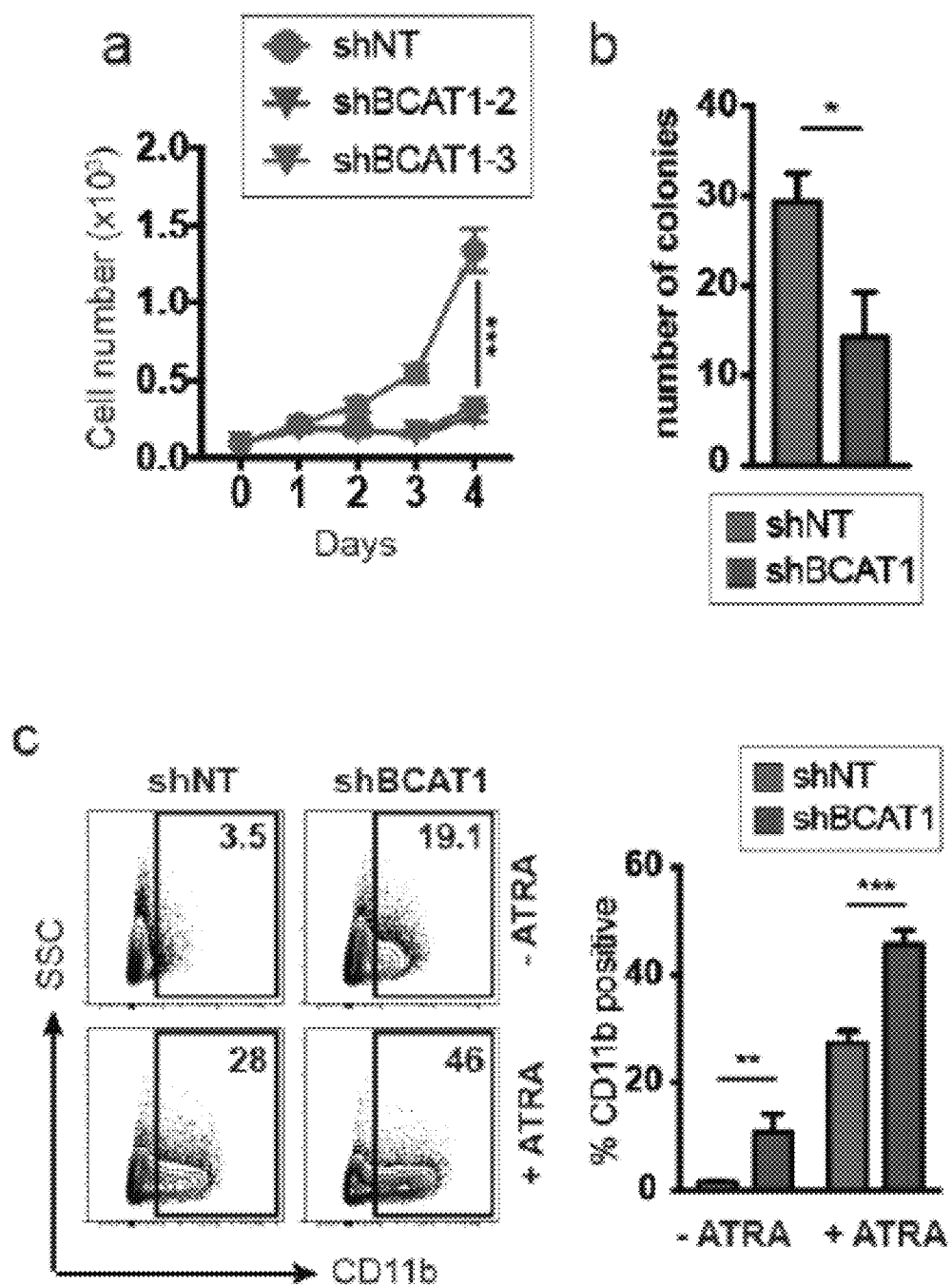

To gain additional mechanistic insight into cellular pathways affected by BCAT1, we utilized the HL-60 AML cell line. Both, defective growth (FIG. 4a) and impaired colony forming capacity (FIG. 4b) upon BCAT1-knockdown were recapitulated and KD-cells showed enhanced myeloid differentiation (FIG. 4c). Gene set enrichment analysis of transcriptome data derived from shBCAT1 and control transduced HL-60 cells revealed HIF1 target genes down-regulated upon BCAT1-KD (FIG. 4d), whereas PU.1 target genes were enriched, molecularly underpinning the differentiation phenotype. Western blot analysis confirmed HIF1 as downstream target of BCAT1 (FIG. 4e), and decreased HIF1 levels were due to enhanced protein degradation since the relative amount of hydroxylated Proline564 was increased after BCAT1 knockdown (FIG. 4f), as intracellular αKG is a co-factor of EGLN1 activity[14]. To inhibit EGLN1 activity, we treated cells with cobalt chloride (Carmeliet Review), which resulted in an attenuated decrease of HIF1 protein levels in BCAT1 knockdown cells (FIG. 4g). Finally, lentiviral overexpression of HIF1 as well as shRNA-mediated knockdown of EGLN1 was sufficient to rescue the proliferation and survival defect after BCAT1-KD (FIG. 4h, i). Together, these analyses place BCAT1 upstream of HIF1 mediating its effect via the αKG-dependent activation of EGLN1. This activation resulted in enhanced degradation of HIF1 protein upon BCAT1 knockdown leading a proliferation and survival defect of these cells. Knockdown of HIF1 is sufficient to abrogate LSC function[16].

Mutations in Isocitrate Dehydroxygenase (IDH) 1 and 2 genes frequently occur in AMLs[17] and result in the production of the oncometabolite 2-hydroxyglutarate (2-HG)[18]. 2-HG acts as competitive inhibitor of αKG-dependent dioxygenases such as TET2[19], thus mimicking a state of low intracellular αKG levels. We therefore hypothesised that BCAT1 expression levels may impact on the clinical outcome only in IDHwt and TET2wt (TET2 mutations are mutually exclusive to IDH mutations[20]) AML patients. Indeed, BCAT1 expression above median (BCAT1$^{high}$) in normal karyotype AML patients devoid of IDH and TET2 mutations was associated with a strikingly shorter overall survival in two independent cohorts (Bullinger and Delwel, GSE14468) (402 days vs. undefined; p=0.0009, HR=2.57 and 306 vs. 1279 days, p=0.0002, HR=2.11) compared to BCAT1$^{low}$ patients. As expected, the BCAT1$^{high}$ group in patients carrying IDH or TET2 mutations had a non-significant trend towards better OS (380 vs. 306 days, p=0.35, HR=0.76 and 1708 vs. 1046 days, p=0.58, HR=0.79) (FIG.

5a). The overall BCAT1 expression level distribution was similar among these groups, which is in contrast to gliomas, in which IDH mutations and BCAT1 expression are mutually exclusive[5]. Similar results were also obtained by analysis of the TCGA[21] dataset. IDH mutations are mutually exclusive to TET2 mutations and both lead to DNA hypermethylation due to reduced activity of the αKG-dependent dioxygenase TET2[20]. We next hypothesised that high BCAT1 expression would lead to DNA hypermethylation comparable to AML samples carrying mutations in IDH or TET2 genes. Indeed, in the TOGA dataset (excluding samples with mutations in the epigenetic modifier DNMT3a) we found a significant positive correlation between BCAT1 expression levels and global DNA methylation in $IDH^{wt}TET2^{wt}$ AML cases, which was not significant and not present in $IDH^{mut}$ and $TET2^{mut}$ cases, respectively (FIG. 5b). Unsupervised hierarchical clustering of the GpG methylation status revealed a close relationship of $IDH^{wt}TET2^{wt}BCAT1^{high}$ AML samples with $IDH^{mut}$ and $TET2^{mut}$ patients, whereas $IDH^{wt}TET2^{wt}BCAT1^{low}$ samples clustered separately (FIG. 5c). Comparing the transcriptomes of $BCAT1^{high}$ and $BCAT1^{low}$ samples revealed a strong enrichment of gene sets characteristic of $IDH^{mut}$ AMLs[22] in $IDH^{wt}TET2^{wt}BCAT1^{high}$ cases in all patient cohorts (FIG. 5d). In addition, enrichment for an LSC signature[5] further supports the role of BCAT1 in LSCs (FIG. 5d). To establish a causal link between high BCAT1 expression, αKG levels and DNA methylation we overexpressed BCAT1 in HL-60 cells. αKG levels significantly decreased (FIG. 5e) and at the transcriptome level we found an enrichment of the $IDH^{mut}$ gene set[22] and the LSC signature in BCAT1 overexpressing cells (FIG. 5f). Prolonged BCAT1-overexpression for 10 weeks (approx. 35 cell doublings) resulted in a clear shift towards DNA hypermethylation (FIG. 5g). In the TCGA data set, 77% of the hypermethylated probes (p<0.001, diffMeth>0.25) between $IDH^{wt}BCAT1^{high}$ and $IDH^{wt}BCAT1^{low}$ AML patients showed hypermethylation also in $IDH^{mut}$ patients (p<0.001, diffMeth >0.25) (FIG. 5h). 1039 (87%) of these 1193 probes were also higher methylated in BCAT1-overexpressing HL-60 cells.

Together, high levels of BCAT1 expression in primary AMLs and overexpression of BCAT1 in HL-60 cells is associated with alterations in DNA methylation characteristic for $IDH^{mut}$ AMLs. A prognostic effect of BCAT1 expression levels was observed only for $IDH^{wt}$ cases, as $IDH^{mut}$ AMLs per se show a reduced activity of αKG-dependent dioxygenases (via competitive inhibition by 2-HG[19]) and lowering of intracellular αKG levels by BCAT1 may not further decrease the activity of these enzymes.

AML patient survival is usually associated with sensitivity to standard chemotherapy[23,24]. In AML cells with long-term BCAT1-overexpression we observed increased resistance to daunorubicin (FIG. 5i). Along these lines, BCAT1 expression was consistently higher (on average 6.6-fold) in the relapse versus the paired diagnostic sample (FIG. 5j).

In summary, our study identifies BCAT1 as a critical enzyme for αKG homeostasis and thus specifically links branched chain amino acids metabolism to epigenetic and post-translational regulation though the regulation of αKG-dependent dioxygenases. BCAT1 acts upstream of mutations in the epigenetic modifiers IDH and TET2 and αKG may act as a naturally occurring tumour suppressor metabolite. While we cannot formally prove that αKG levels are lower in BCAT1high primary AML cells due to technical limitations our results strongly support that causative link. A recent publication suggested LSC fractions to be hypomethylated[25]. However, when analysing the subgroup of cases with a hierarchical organisation, i.e. presence of LSC+ and LSC− populations within one individual, LSC+ populations were more methylated, in line with our results.

While high intracellular αKG levels maintain the pluripotenty of mouse embryonic stem cells[26] leukemia stem cells maintain high BCAT1 levels to suppress αKG. For the future, therapeutic strategies to increase αKG in order to compromise LSC function i.e. by inhibition of BCAT1, may lead to lower relapse rates and improved survival of AML patients.

Example 2

Determination of BCAT1 Expression Levels

The BCAT1 expression level and the determination of $BCAT1^{high}$ or $BCAT1^{low}$ status, in particular by using the ratio of BCAT1/ABL1 expression, can be determined by qPCR, particularly by qRT-PCR as shown in the literature, e.g. as in Tönjes et al., Nat Med. 2013 July; 19(7): 901-908.

In particular, total RNA can be extracted using the AllPrep DNA/RNA/Protein Mini Kit (Qiagen) according to the manufacturer's instructions. FirstChoice Human Brain Reference Total RNA from Ambion can serve as the normal brain RNA pool. Total RNA (500 ng) can be reverse transcribed using random primers and superscript II (Invitrogen) according to the manufacturer's instructions. Each cDNA sample can be analyzed in triplicate with the Applied Biosystems Prism 7900HT Fast Real-Time PCR System using Absolute SYBR Green ROX Mix (ABgene). The relative amount of specific BCAT1 mRNA can be normalized to ABL1 mRNA. Alternatively, the relative amount of specific BCAT1 mRNA can be normalized to ARF1, B2M or TBP mRNA. Primer sequences are shown below in Table 1.

TABLE 1

Primer Sequences primers

| | | |
|---|---|---|
| BCAT1 (all isoforms) | Forward | CAACTATGGAGAATGGTCCTAAGCT |
| | Reverse | TGTCCAGTCGCTCTCTTCTCTTC |
| BCAT1 T1 (ENST00000261192) | Forward | GCTACGACCCTTGGGATCT |
| BCAT1 T4 (ENST00000539282) | Forward | GTGCCACTGCCGCTCTCT |
| BCAT1 T6 (ENST00000538118) | Forward | TGGTTGTCTGAGCCTCCTTT |
| BCAT1 Exon 2 | Reverse | AAGTCCCCACCACCTCTTTT |
| BCAT1 Exon 5 | Reverse | CCCATTCTTGATCCAATTTCA |
| HEY1 | Forward | CGAGCTGGACGAGACCAT |
| | Reverse | GAGCCGAACTCAAGTTTCCA |
| ARF | Forward | GACCACGATCCTCTACAAGC |
| | Reverse | TCCCACACAGTGAAGCTGATG |
| B2M | Forward | ACTGAATTCACCCCCACTGA |
| | Reverse | CCTCCATGATGCTGCTTACA |
| TBP | Forward | GAACCACGGCACTGATTTTC |
| | Reverse | CCCCACCATGTTCTGAATCT |
| ABL1 | Forward | TTCAGCGGCCAGTAGCATCTGACTT |
| | Reverse | GATGTAGTTGCTTGGGACCCA |

REFERENCES

1. Tonjes, M. et al. BCAT1 promotes cell proliferation through amino acid catabolism in gliomas carrying wild-type IDH1. *Nat Med* 19, 901-908, doi:10.1038/nm.3217 (2013).
2. Wang, Z. Q. et al. BCAT1 expression associates with ovarian cancer progression: possible implications in altered disease metabolism. *Oncotarget* 6, 31522-31543, doi:10.18632/oncotarget.5159 (2015).
3. Zheng, Y. H. et al. BCAT1, a key prognostic predictor of hepatocellular carcinoma, promotes cell proliferation and induces chemoresistance to cisplatin. *Liver Int* 36, 1836-1847, doi:10.1111/liv.13178 (2016).
4. Mayers, J. R. et al. Tissue of origin dictates branched-chain amino acid metabolism in mutant Kras-driven cancers. *Science* 353, 1161-1165, doi:10.1126/science.aaf5171 (2016).
5. Eppert, K. et al. Stem cell gene expression programs influence clinical outcome in human leukemia. *Nat Med* 17, 1086-1093, doi:10.1038/nm.2415 (2011).
6. Sarry, J. E. et al. Human acute myelogenous leukemia stem cells are rare and heterogeneous when assayed in NOD/SCID/IL2Rgammac-deficient mice. *J Clin Invest* 121, 384-395, doi:10.1172/JCI41495 (2011).
7. Ng, S. W. et al. A 17-gene sternness score for rapid determination of risk in acute leukaemia. *Nature* 540, 433-437, doi:10.1038/nature20598 (2016).
8. Guan, Y., Gerhard, B. & Hogge, D. E. Detection, isolation, and stimulation of quiescent primitive leukemic progenitor cells from patients with acute myeloid leukemia (AML). *Blood* 101, 3142-3149, doi:10.1182/blood-2002-10-3062 (2003).
9. Oburoglu, L. et al. Glucose and glutamine metabolism regulate human hematopoietic stern cell lineage specification. *Cell Stem Cell* 15, 169-184, doi:10.1016/j.stem.2014.06.002 (2014).
10. Ichihara, A. & Koyama, E. Transaminase of branched chain amino acids. I. Branched chain amino acids-alpha-ketoglutarate transaminase. *J Biochem* 59, 160-169 (1966).
11. Green, C. R. et al. Branched-chain amino acid catabolism fuels adipocyte differentiation and lipogenesis. *Nat Chem Biol* 12, 15-21, doi:10.1038/nchembio.1961 (2016).
12. Loenarz, C. & Schofield, C. J. Expanding chemical biology of 2-oxoglutarate oxygenases. *Nat Chem Biol* 4, 152-156, doi:10.1038/nchembio0308-152 (2008).
13. Kaelin, W. G., Jr. & McKnight, S. L. Influence of metabolism on epigenetics and disease. *Cell* 153, 56-69, doi:10.1016/j.cell.2013.03.004 (2013).
14. Epstein, A. C. et al. C. elegans EGL-9 and mammalian homologs define a family of dioxygenases that regulate HIF by prolyl hydroxylation. *Cell* 107, 43-54 (2001).
15. Tahiliani, M. et al. Conversion of 5-methylcytosine to 5-hydroxymethylcytosine in mammalian DNA by MLL partner TET1. *Science* 324, 930-935, doi:10.1126/science.1170116 (2009).
16. Wang, Y., Liu, Y., Malek, S. N., Zheng, P. & Liu, Y. Targeting HIF1alpha eliminates cancer stem cells in hematological malignancies. *Cell Stem Cell* 8, 399-411, doi:10.1016/j.stem.2011.02.006 (2011).
17. Paschka, P. et al. IDH1 and IDH2 mutations are frequent genetic alterations in acute myeloid leukemia and confer adverse prognosis in cytogenetically normal acute myeloid leukemia with NPM1 mutation without FLT3 internal tandem duplication. *J Clin Oncol* 28, 3636-3643, doi:10.1200/JC0.2010.28.3762 (2010).
18. Dang, L. et al. Cancer-associated IDH1 mutations produce 2-hydroxyglutarate. *Nature* 462, 739-744, doi: 10.1038/nature08617 (2009).
19. Xu, W. et al. Oncometabolite 2-hydroxyglutarate is a competitive inhibitor of alpha-ketoglutarate-dependent dioxygenases. *Cancer Cell* 19, 17-30, doi:10.1016/j.ccr.2010.12.014 (2011).
20. Figueroa, M. E. et al. Leukemic IDH1 and IDH2 mutations result in a hypermethylation phenotype, disrupt TET2 function, and impair hematopoietic differentiation. *Cancer Cell* 18, 553-567, doi:10.1016/j.ccr.2010.11.015 (2010).
21. Cancer Genome Atlas Research, N. Genomic and epigenomic landscapes of adult de novo acute myeloid leukemia. *N Engl J Med* 368, 2059-2074, doi:10.1056/NEJMoa1301689 (2013).
22. Marcucci, G. et al. IDH1 and IDH2 gene mutations identify novel molecular subsets within de novo cytogenetically normal acute myeloid leukemia: a Cancer and Leukemia Group B study. *J Clin Oncol* 28, 2348-2355, doi:10.1200/JC0.2009.27.3730 (2010).
23. Elliott, M. A. et al. Early peripheral blood blast clearance during induction chemotherapy for acute myeloid leukemia predicts superior relapse-free survival. *Blood* 110, 4172-4174, doi:10.1182/blood-2007-07-104091 (2007).
24. Kern, W. et al. Early blast clearance by remission induction therapy is a major independent prognostic factor for both achievement of complete remission and long-term outcome in acute myeloid leukemia: data from the German AML Cooperative Group (AMLCG) 1992 Trial. *Blood* 101, 64-70, doi:10.1182/blood-2002-02-0532 (2003).
25. Jung, N., Dai, B., Gentles, A. J., Majeti, R. & Feinberg, A. P. An LSC epigenetic signature is largely mutation independent and implicates the HOXA cluster in AML pathogenesis. *Nat Commun* 6, 8489, doi:10.1038/ncomms9489 (2015).

Carey, B. W., Finley, L. W., Cross, J. R., Allis, C. D. & Thompson, C. B. Intracellular alpha-ketoglutarate maintains the pluripotency of embryonic stem cells. *Nature* 518, 413-416, doi:10.1038/nature13981 (2015).

The invention claimed is:

1. A method of treating Acute Myeloid Leukemia (AML) in a patient suffering from AML, wherein said AML is characterized by BCAT1$^{high}$ expression and IDH$^{wt}$TET$^{wt}$, comprising the step of administering a compound that increases intracellular levels of α-ketoglutarate, wherein the compound is (i) a BCAT1 inhibitor selected from: an antisense molecule, wherein said antisense molecule consists of a nucleotide sequence from 12 to 25 nucleotides, wherein the sequence corresponds to the antisense strand of the nucleic acid sequence coding for BCAT1, an siRNA molecule, wherein said siRNA molecule has between 20 and 25 based pairs being complementary to the mRNA coding for BCAT1, and a small molecule inhibitor selected from 1-(aminomethyl) cyclohexaneacetic acid, compound 2 and compound 8

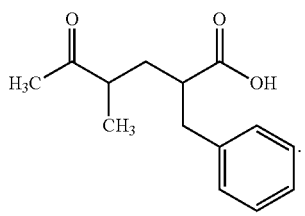

Compound 2

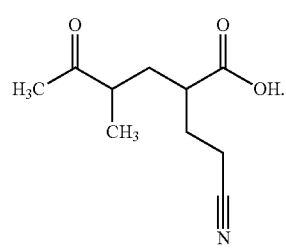

Compound 8 or (ii) wherein said compound is selected from α-ketoglutaric acid, a mono- or dibasic salt of α-ketoglutaric acid, or a derivative of α-ketoglutaric acid having at least one of its carboxylic acid groups derivatized as ester or amide.

2. The method of claim 1, wherein the compound is selected from 2-oxo-pentanedioic acid, 1-hexyl ester, 2-oxo-pentanedioic acid, 1-octyl ester, benzyl-α-ketoglutarate ester and 3-trifluoromethylbenzyl-α-ketoglutarate ester.

3. The method of claim 1, wherein said BCAT1$^{high}$ expression is determined by quantitative PCR.

4. The method of claim 3, wherein said BCAT1$^{high}$ expression is determined in relation to the expression of a reference.

5. The method of claim 1, wherein the compound in (ii) is a mono-ester of α-ketoglutaric acid or a di-ester of α-ketoglutaric acid.

6. The method of claim 4, wherein said reference is ABL1.

7. The method of claim 6, wherein BCAT1$^{high}$ expression is characterized by a ratio of BCAT1/ABL1 of greater than 0.90.

* * * * *

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: artificial primer sequence

```
<400> SEQUENCE: 1
caactatgga gaatggtcct aagct                                      25

<210> SEQ ID NO 2
<211> LENGTH: 23
<212> TYPE: DNA
<213> ORGANISM: Artificial Sequence
<220> FEATURE:
<223> OTHER INFORMATION: artificial primer sequence

<400> SEQUENCE: 2
tgtccagtcg ctctcttctc ttc                                        23

<210> SEQ ID NO 3
<211> LENGTH: 19
<212> TYPE: DNA
<213> ORGANISM: Artificial Sequence
<220> FEATURE:
<223> OTHER INFORMATION: artificial primer sequence

<400> SEQUENCE: 3
gctacgaccc ttgggatct                                             19

<210> SEQ ID NO 4
<211> LENGTH: 18
<212> TYPE: DNA
<213> ORGANISM: Artificial Sequence
<220> FEATURE:
<223> OTHER INFORMATION: artificial primer sequence

<400> SEQUENCE: 4
gtgccactgc cgctctct                                              18

<210> SEQ ID NO 5
<211> LENGTH: 20
<212> TYPE: DNA
<213> ORGANISM: Artificial Sequence
<220> FEATURE:
<223> OTHER INFORMATION: artificial primer sequence

<400> SEQUENCE: 5
tggttgtctg agcctccttt                                            20

<210> SEQ ID NO 6
<211> LENGTH: 20
<212> TYPE: DNA
<213> ORGANISM: Artificial Sequence
<220> FEATURE:
<223> OTHER INFORMATION: artificial primer sequence

<400> SEQUENCE: 6
aagtccccac cacctctttt                                            20

<210> SEQ ID NO 7
<211> LENGTH: 21
<212> TYPE: DNA
<213> ORGANISM: Artificial Sequence
<220> FEATURE:
<223> OTHER INFORMATION: artificial primer sequence

<400> SEQUENCE: 7
cccattcttg atccaatttc a                                          21

<210> SEQ ID NO 8
<211> LENGTH: 18
```

```
<212> TYPE: DNA
<213> ORGANISM: Artificial Sequence
<220> FEATURE:
<223> OTHER INFORMATION: artificial primer sequence

<400> SEQUENCE: 8
cgagctggac gagaccat                                              18

<210> SEQ ID NO 9
<211> LENGTH: 20
<212> TYPE: DNA
<213> ORGANISM: Artificial Sequence
<220> FEATURE:
<223> OTHER INFORMATION: artificial primer sequence

<400> SEQUENCE: 9
gagccgaact caagtttcca                                            20

<210> SEQ ID NO 10
<211> LENGTH: 20
<212> TYPE: DNA
<213> ORGANISM: Artificial Sequence
<220> FEATURE:
<223> OTHER INFORMATION: artificial primer sequence

<400> SEQUENCE: 10
gaccacgatc ctctacaagc                                            20

<210> SEQ ID NO 11
<211> LENGTH: 21
<212> TYPE: DNA
<213> ORGANISM: Artificial Sequence
<220> FEATURE:
<223> OTHER INFORMATION: artificial primer sequence

<400> SEQUENCE: 11
tcccacacag tgaagctgat g                                          21

<210> SEQ ID NO 12
<211> LENGTH: 20
<212> TYPE: DNA
<213> ORGANISM: Artificial Sequence
<220> FEATURE:
<223> OTHER INFORMATION: artificial primer sequence

<400> SEQUENCE: 12
actgaattca cccccactga                                            20

<210> SEQ ID NO 13
<211> LENGTH: 20
<212> TYPE: DNA
<213> ORGANISM: Artificial Sequence
<220> FEATURE:
<223> OTHER INFORMATION: artificial primer sequence

<400> SEQUENCE: 13
cctccatgat gctgcttaca                                            20

<210> SEQ ID NO 14
<211> LENGTH: 20
<212> TYPE: DNA
<213> ORGANISM: Artificial Sequence
<220> FEATURE:
<223> OTHER INFORMATION: artificial primer sequence
```

```
<400> SEQUENCE: 14
gaaccacggc actgattttc                                              20

<210> SEQ ID NO 15
<211> LENGTH: 20
<212> TYPE: DNA
<213> ORGANISM: Artificial Sequence
<220> FEATURE:
<223> OTHER INFORMATION: artificial primer sequence

<400> SEQUENCE: 15
ccccaccatg ttctgaatct                                              20

<210> SEQ ID NO 16
<211> LENGTH: 25
<212> TYPE: DNA
<213> ORGANISM: Artificial Sequence
<220> FEATURE:
<223> OTHER INFORMATION: artificial primer sequence

<400> SEQUENCE: 16
ttcagcggcc agtagcatct gactt                                        25

<210> SEQ ID NO 17
<211> LENGTH: 21
<212> TYPE: DNA
<213> ORGANISM: Artificial Sequence
<220> FEATURE:
<223> OTHER INFORMATION: artificial primer sequence

<400> SEQUENCE: 17
gatgtagttg cttgggaccc a                                            21
```